US010481111B2

(12) United States Patent
Hench et al.

(10) Patent No.: US 10,481,111 B2
(45) Date of Patent: Nov. 19, 2019

(54) CALIBRATION OF A SMALL ANGLE X-RAY SCATTEROMETRY BASED METROLOGY SYSTEM

(71) Applicant: KLA-Tencor Corporation, Milpitas, CA (US)

(72) Inventors: John Hench, Los Gatos, CA (US); Antonio Gellineau, Santa Clara, CA (US); Nikolay Artemiev, Berkeley, CA (US); Joseph A. Di Regolo, Livermore, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 201 days.

(21) Appl. No.: 15/789,992

(22) Filed: Oct. 21, 2017

(65) Prior Publication Data

US 2018/0113084 A1 Apr. 26, 2018

Related U.S. Application Data

(60) Provisional application No. 62/411,152, filed on Oct. 21, 2016.

(51) Int. Cl.
*G01N 23/20* (2018.01)
*G01N 23/201* (2018.01)
(Continued)

(52) U.S. Cl.
CPC ......... *G01N 23/201* (2013.01); *G01N 23/083* (2013.01); *G01N 23/20083* (2013.01);
(Continued)

(58) Field of Classification Search
CPC ............... G01N 23/201; G01N 23/083; G01N 23/20083; G01N 2223/054; G01N 2223/303; G21K 1/067
See application file for complete search history.

(56) References Cited

U.S. PATENT DOCUMENTS 5,608,526 A 3/1997 Piwonka-Corle et al.
5,859,424 A 1/1999 Norton et al.
(Continued)

FOREIGN PATENT DOCUMENTS

JP 2016-516307 A 6/2016
KR 10-2002-0034988 5/2002
WO 2000055572 9/2000

OTHER PUBLICATIONS

International Search Report dated Feb. 2, 2018, for PCT Application No. PCT/US2017/057770 filed on Oct. 22, 2017 by KLA-Tencor Corporation, 3 pages.

*Primary Examiner* — David P Porta
*Assistant Examiner* — Djura Malevic
(74) *Attorney, Agent, or Firm* — Spano Law Group; Joseph S. Spano

(57) ABSTRACT

Methods and systems for calibrating the location of x-ray beam incidence onto a specimen in an x-ray scatterometry metrology system are described herein. The precise location of incidence of the illumination beam on the surface of the wafer is determined based on occlusion of the illumination beam by two or more occlusion elements. The center of the illumination beam is determined based on measured values of transmitted flux and a model of the interaction of the beam with each occlusion element. The position of the axis of rotation orienting a wafer over a range of angles of incidence is adjusted to align with the surface of wafer and intersect the illumination beam at the measurement location. A precise offset value between the normal angle of incidence of the illumination beam relative to the wafer surface and the zero angle of incidence as measured by the specimen positioning system is determined.

22 Claims, 10 Drawing Sheets

(51) Int. Cl.
*G01N 23/083* (2018.01)
*G21K 1/06* (2006.01)

(52) U.S. Cl.
CPC . *G01N 2223/054* (2013.01); *G01N 2223/303* (2013.01); *G21K 1/067* (2013.01)

(56) References Cited

U.S. PATENT DOCUMENTS

| | | | |
|---|---|---|---|
| 6,023,338 A | 2/2000 | Bareket | |
| 6,429,943 B1 | 8/2002 | Opsal et al. | |
| 6,716,646 B1 | 4/2004 | Wright et al. | |
| 6,778,275 B2 | 8/2004 | Bowes | |
| 6,787,773 B1 | 9/2004 | Lee | |
| 6,992,764 B1 | 1/2006 | Yang et al. | |
| 7,242,477 B2 | 7/2007 | Mieher et al. | |
| 7,321,426 B1 | 1/2008 | Poslavsky et al. | |
| 7,406,153 B2 | 7/2008 | Berman | |
| 7,478,019 B2 | 1/2009 | Zangooie et al. | |
| 7,626,702 B2 | 12/2009 | Ausschnitt et al. | |
| 7,656,528 B2 | 2/2010 | Abdulhalim et al. | |
| 7,659,975 B1 | 2/2010 | Ramani et al. | |
| 7,826,071 B2 | 11/2010 | Shchegrov et al. | |
| 7,842,933 B2 | 11/2010 | Shur et al. | |
| 7,873,585 B2 | 1/2011 | Izikson | |
| 7,929,667 B1 | 4/2011 | Zhuang et al. | |
| 7,933,026 B2 | 4/2011 | Opsal et al. | |
| 8,068,662 B2 | 11/2011 | Zhang et al. | |
| 8,138,498 B2 | 3/2012 | Ghinovker | |
| 8,502,987 B1 | 8/2013 | Chipman | |
| 9,726,624 B2 * | 8/2017 | Ryan | G01N 23/2055 |
| 2002/0080344 A1 | 6/2002 | Tomita et al. | |
| 2003/0021465 A1 | 1/2003 | Adel et al. | |
| 2006/0213537 A1* | 9/2006 | Atalla | H01L 21/67028 134/18 |
| 2007/0081151 A1 | 4/2007 | Shortt et al. | |
| 2007/0221842 A1 | 9/2007 | Morokuma et al. | |
| 2009/0123892 A1* | 5/2009 | Sogo | A61C 11/00 433/213 |
| 2009/0152463 A1 | 6/2009 | Toyoda et al. | |
| 2011/0266440 A1 | 11/2011 | Boughorbel et al. | |
| 2012/0044486 A1 | 2/2012 | Chen et al. | |
| 2012/0292502 A1 | 11/2012 | Langer et al. | |
| 2013/0208279 A1 | 8/2013 | Smith | |
| 2013/0304424 A1 | 11/2013 | Bakeman et al. | |
| 2014/0019097 A1 | 1/2014 | Bakeman et al. | |
| 2014/0111791 A1 | 4/2014 | Manassen et al. | |
| 2014/0166862 A1 | 6/2014 | Flock | |
| 2014/0172394 A1 | 6/2014 | Kuznetsov et al. | |
| 2014/0222380 A1 | 8/2014 | Kuznetsov et al. | |
| 2014/0297211 A1 | 10/2014 | Pandev et al. | |
| 2015/0110249 A1 | 4/2015 | Bakeman et al. | |
| 2015/0117610 A1 | 4/2015 | Veldman et al. | |
| 2015/0204664 A1 | 7/2015 | Bringoltz et al. | |
| 2015/0270023 A1 | 9/2015 | Adler | |
| 2015/0300965 A1 | 10/2015 | Sezginer et al. | |
| 2016/0202193 A1 | 7/2016 | Hench et al. | |
| 2016/0320319 A1 | 11/2016 | Hench et al. | |
| 2017/0167862 A1* | 6/2017 | Dziura | G01N 23/2055 |
| 2018/0106735 A1* | 4/2018 | Gellineau | G01B 15/00 |

\* cited by examiner

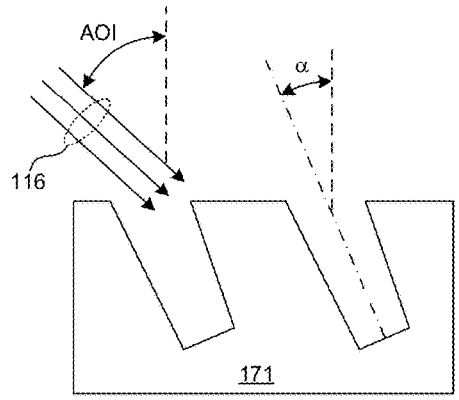
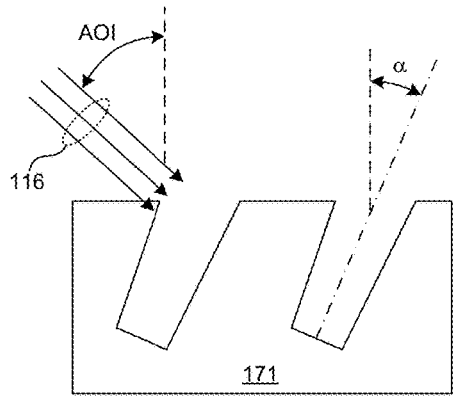
FIG. 9A  FIG. 9B
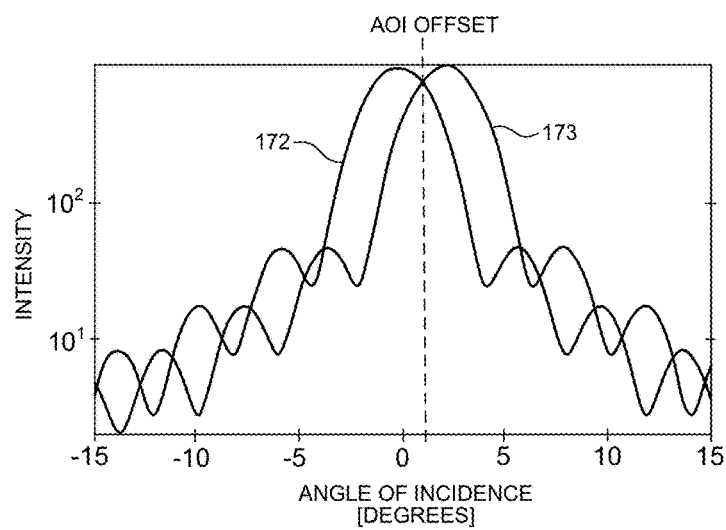
FIG. 10

CALIBRATION OF A SMALL ANGLE X-RAY SCATTEROMETRY BASED METROLOGY SYSTEM

CROSS REFERENCE TO RELATED APPLICATION

The present application for patent claims priority under 35 U.S.C. § 119 from U.S. provisional patent application Ser. No. 62/411,152, filed Oct. 21, 2016, the subject matter of which is incorporated herein by reference in its entirety.

TECHNICAL FIELD

The described embodiments relate to x-ray metrology systems and methods, and more particularly to methods and systems for improved measurement accuracy.

BACKGROUND INFORMATION

Semiconductor devices such as logic and memory devices are typically fabricated by a sequence of processing steps applied to a specimen. The various features and multiple structural levels of the semiconductor devices are formed by these processing steps. For example, lithography among others is one semiconductor fabrication process that involves generating a pattern on a semiconductor wafer. Additional examples of semiconductor fabrication processes include, but are not limited to, chemical-mechanical polishing, etch, deposition, and ion implantation. Multiple semiconductor devices may be fabricated on a single semiconductor wafer and then separated into individual semiconductor devices.

Metrology processes are used at various steps during a semiconductor manufacturing process to detect defects on wafers to promote higher yield. A number of metrology based techniques including scatterometry and reflectometry implementations and associated analysis algorithms are commonly used to characterize critical dimensions, film thicknesses, composition and other parameters of nanoscale structures.

Traditionally, scatterometry critical dimension measurements are performed on targets consisting of thin films and/or repeated periodic structures. During device fabrication, these films and periodic structures typically represent the actual device geometry and material structure or an intermediate design. As devices (e.g., logic and memory devices) move toward smaller nanometer-scale dimensions, characterization becomes more difficult. Devices incorporating complex three-dimensional geometry and materials with diverse physical properties contribute to characterization difficulty. For example, modern memory structures are often high-aspect ratio, three-dimensional structures that make it difficult for optical radiation to penetrate to the bottom layers. Optical metrology tools utilizing infrared to visible light can penetrate many layers of translucent materials, but longer wavelengths that provide good depth of penetration do not provide sufficient sensitivity to small anomalies. In addition, the increasing number of parameters required to characterize complex structures (e.g., FinFETs), leads to increasing parameter correlation. As a result, the parameters characterizing the target often cannot be reliably decoupled with available measurements.

In one example, longer wavelengths (e.g. near infrared) have been employed in an attempt to overcome penetration issues for 3D FLASH devices that utilize polysilicon as one of the alternating materials in the stack. However, the mirror like structure of 3D FLASH intrinsically causes decreasing light intensity as the illumination propagates deeper into the film stack. This causes sensitivity loss and correlation issues at depth. In this scenario, SCD is only able to successfully extract a reduced set of metrology dimensions with high sensitivity and low correlation.

In another example, opaque, high-k materials are increasingly employed in modern semiconductor structures. Optical radiation is often unable to penetrate layers constructed of these materials. As a result, measurements with thin-film scatterometry tools such as ellipsometers or reflectometers are becoming increasingly challenging.

In response to these challenges, more complex optical metrology tools have been developed. For example, tools with multiple angles of illumination, shorter illumination wavelengths, broader ranges of illumination wavelengths, and more complete information acquisition from reflected signals (e.g., measuring multiple Mueller matrix elements in addition to the more conventional reflectivity or ellipsometric signals) have been developed. However, these approaches have not reliably overcome fundamental challenges associated with measurement of many advanced targets (e.g., complex 3D structures, structures smaller than 10 nm, structures employing opaque materials) and measurement applications (e.g., line edge roughness and line width roughness measurements).

Atomic force microscopes (AFM) and scanning-tunneling microscopes (STM) are able to achieve atomic resolution, but they can only probe the surface of the specimen. In addition, AFM and STM microscopes require long scanning times. Scanning electron microscopes (SEM) achieve intermediate resolution levels, but are unable to penetrate structures to sufficient depth. Thus, high-aspect ratio holes are not characterized well. In addition, the required charging of the specimen has an adverse effect on imaging performance. X-ray reflectometers also suffer from penetration issues that limit their effectiveness when measuring high aspect ratio structures.

To overcome penetration depth issues, traditional imaging techniques such as TEM, SEM etc., are employed with destructive sample preparation techniques such as focused ion beam (FIB) machining, ion milling, blanket or selective etching, etc. For example, transmission electron microscopes (TEM) achieve high resolution levels and are able to probe arbitrary depths, but TEM requires destructive sectioning of the specimen. Several iterations of material removal and measurement generally provide the information required to measure the critical metrology parameters throughout a three dimensional structure. But, these techniques require sample destruction and lengthy process times. The complexity and time to complete these types of measurements introduces large inaccuracies due to drift of etching and metrology steps. In addition, these techniques require numerous iterations which introduce registration errors.

Transmission, Small-Angle X-Ray Scatterometry (T-SAXS) systems have shown promise to address challenging measurement applications. Current T-SAXS tools employ beam forming slits to form the illumination beam incident on the specimen under measurement. A beam divergence shaping slit is located in the beam path before or after the focusing optics to define the divergence angle of the beam. A beam shaping slit is located in the beam path after the beam divergence shaping slit to define the size of the beam spot incident on the wafer. Furthermore, T-SAXS measurements are performed over large ranges of angle of incidence. Registration of the location of the incident beam on metrology targets under measurement over a large range of angles of incidence is required to ensure reliable measurements.

To further improve device performance, the semiconductor industry continues to focus on vertical integration, rather than lateral scaling. Thus, accurate measurement of complex, fully three dimensional structures is crucial to ensure viability and continued scaling improvements. Future metrology applications present challenges for metrology due to increasingly small resolution requirements, multi-parameter correlation, increasingly complex geometric structures including high aspect ratio structures, and increasing use of opaque materials. Thus, methods and systems for improved T-SAXS measurements are desired.

SUMMARY

Methods and systems for calibrating the location of x-ray beam incidence onto a specimen in a Transmission, Small-Angle X-ray Scatterometry (T-SAXS) metrology system are described herein. Practical T-SAXS measurements in a semiconductor manufacturing environment require measurements over a large range of angles of incidence and azimuth with respect to the surface of a specimen (e.g., semiconductor wafer) with a small beam spot size (e.g., less than 50 micrometers across the effective illumination spot). Calibrations that accurately locate the illumination beam on the desired target area on the surface of a semiconductor wafer over the full range of incidence and azimuth angles are described herein.

In one aspect, the precise location of incidence of the illumination beam in two dimensions in the plane of the surface of the wafer is determined based on the interaction of the illumination beam with two or more occlusion elements. The center of the illumination beam is determined based on measured values of transmitted flux and a model of the interaction of the beam with the material and geometry of the occlusion element.

In a further aspect, the position of incidence of the illumination beam is determined at any location on the wafer based on images measured by an alignment camera. The alignment camera registers the relative position of the illumination beam with respect to a feature of the occlusion element (e.g., edge or fiducial) and transfers that registration to one or more locations on the surface of the wafer. In addition, the position of the wafer in the Z-direction with respect to the Z-location of occlusion element is measured by changing the focus position of alignment camera until the lithographic features on the surface of wafer come into precise focus. The change i-sin focus position is indicative of the difference in Z-position between the occlusion element and the imaged location on the wafer.

In some embodiments, an occlusion element is a knife edge structure. A knife edge structure is typically a thin, sharpened dense high-Z material such as tungsten carbide, with a straight edge that is oriented perpendicular to the direction of position to be calibrated. In addition, the surface of the knife edge is coincident with the surface of the wafer. This enables the alignment camera to focus on the same plane as the wafer, ensuring a good match between measured beam location at the wafer and the reference beam location at the knife edge as measured by the alignment camera.

In some embodiments, the occlusion element is a precision cylinder of known diameter. In these embodiments, the occlusion of the beam is offset in the Z-direction by the radius of the cylinder. In these embodiments, an additional surface coincident with the central axis of the cylinder and marked with a fiducial reference mark is advantageous to refer the camera frame to the axis and radius of the cylindrical occlusion element. In these embodiments, the central axis of the cylindrical occlusion element is coincident with the surface of the wafer, and oriented perpendicular to the direction of position to be calibrated.

In another aspect, the position of the axis of rotation associated with orienting a wafer over a range of angles of incidence is aligned to be co-planar with the surface of wafer and intersect the illumination beam at the measurement location to avoid excessive drift of the illumination spot over the range of angle of incidence.

In some embodiments, the calibration of the position of the axis of rotation is achieved by aligning the center of the illumination beam with an occluding element and measuring transmitted flux at a plurality of different angles of incidence. The apparent motion of the occlusion element is determined from the measured flux based on the chosen occlusion model. A geometric model maps the apparent motion of the occlusion element to adjustments in stage configuration to achieve the desired alignment.

In some other embodiments, the calibration of the position of the axis of rotation is achieved by locating a high-resolution x-ray camera with a focal plane aligned with the wafer plane of the wafer stage. The position of the illumination spot at the wafer plane is measured by the high resolution x-ray camera while the stage is rotated over a large range of angles of incidence. A mapping of the position of the illumination spot at the wafer plane as a function of the angle of incidence is generated based on the measurements.

In some other embodiments, the calibration of the position of the axis of rotation of the stage reference frame is achieved by locating a small target on a wafer having a high diffraction efficiency. The strength of the diffracted orders is measured while the stage is rotated over a large range of angles of incidence. The strength of the diffracted orders is indicative of the misalignment between the illumination spot and the target as a function of angle of incidence. A mapping of the misalignment as a function of the angle of incidence is generated based on the measurements.

In another aspect, a precise measurement of an AOI offset value between the normal angle of incidence of the illumination beam relative to the wafer surface and the zero angle of incidence as measured by the specimen positioning system is determined.

In some embodiments, the AOI offset value is determined based on absorption measurements over a range of AOIs. In some embodiments, the AOI offset value is determined based on measurements of diffraction orders scattered from a calibration grating at two azimuth angles separated by 180 degrees.

In another aspect, a precise measurement of an azimuth offset value between the zero azimuth angle of the wafer surface with respect to the illumination beam and the zero azimuth angle as measured by the specimen positioning system is determined. In addition, a precise measurement of an offset value between the center of the wafer surface and the center of rotation of rotary stage is determined.

In another aspect, a precise calibration of the azimuth angle offset between wafer coordinates and stage coordinates is based on the position of the diffraction orders associated with measurements of a calibration grating having known response characteristics at one or more azimuth angles.

In another aspect, the detector is calibrated with respect to the stage and the azimuth angle is calibrated with respect to stage simultaneously using multiple, calibrated angles of incidence along with well-known formulae for conical diffraction.

In some embodiments, a beam shaping slit mechanism rotates about the beam axis in coordination with the orientation of the specimen to optimize the profile of the incident beam for each angle of incidence, azimuth angle, or both. In this manner, the beam shape is matched to the shape of the metrology target. Unfortunately, imperfections in the rotary actuator cause the beam shaping slit mechanism to precess about the axis of illumination beam. This causes the location of incidence of illumination beam to drift for different azimuth angles and corresponding beam slit angles.

In a further aspect, a calibration map of X-Y stage offsets is determined based on measurements of the location of incidence of illumination beam for a range of azimuth angles and corresponding beam slit angles.

In some embodiments, the measurements are performed by an x-ray camera having a focal plane at the location of the wafer surface. In some other embodiments, a calibration map of X-Y stage offsets is determined based on measurements of a small target by the detector for a range of azimuth angles and corresponding beam slit angles.

In another aspect, the shape of the surface of the wafer in the Z-direction is mapped using any of the alignment camera, an optical proximity sensor, a capacitive proximity sensor, or any other suitable proximity sensor.

In a further aspect, Z-actuators are controlled to adjust wafer Z-position, Rx orientation, Ry orientation, or any combination thereof, in response to the shape of the surface of the wafer at the location of incidence of illumination beam 116.

In another further aspect, Z-actuators are controlled to adjust the wafer Z-position, Rx orientation, Ry orientation, or any combination thereof, to align the axis of rotation in azimuth with the stage reference frame such that a specific target remains in focus of the alignment camera over a range of azimuth angles.

The foregoing is a summary and thus contains, by necessity, simplifications, generalizations and omissions of detail; consequently, those skilled in the art will appreciate that the summary is illustrative only and is not limiting in any way. Other aspects, inventive features, and advantages of the devices and/or processes described herein will become apparent in the non-limiting detailed description set forth herein.

BRIEF DESCRIPTION OF THE DRAWINGS

FIG. 9A depicts a grating structure 171 measured by T-SAXS system 100 at an azimuth angle of zero.

FIG. 9B depicts the same grating structure 171 measured by T-SAXS system 100 at an azimuth angle of 180 degrees.

FIG. 10 depicts a plot indicative of measured intensity of one diffraction order detected by detector 119 for a measurement 172 performed at a zero azimuth angle and another measurement 173 performed at an azimuth angle of 180 degrees.

DETAILED DESCRIPTION

Reference will now be made in detail to background examples and some embodiments of the invention, examples of which are illustrated in the accompanying drawings.

Methods and systems for calibrating the location of x-ray beam incidence onto a specimen in a Transmission, Small-Angle X-ray Scatterometry (T-SAXS) metrology system are described herein. Practical T-SAXS measurements in a semiconductor manufacturing environment require measurements over a large range of angles of incidence and azimuth with respect to the surface of a specimen (e.g., semiconductor wafer) with a small beam spot size (e.g., less than 50 micrometers across the effective illumination spot). Calibrations are that accurately locate the illumination beam on the desired target area on the surface of a semiconductor wafer over the full range of incidence and azimuth angles are presented herein.

Figure 1:
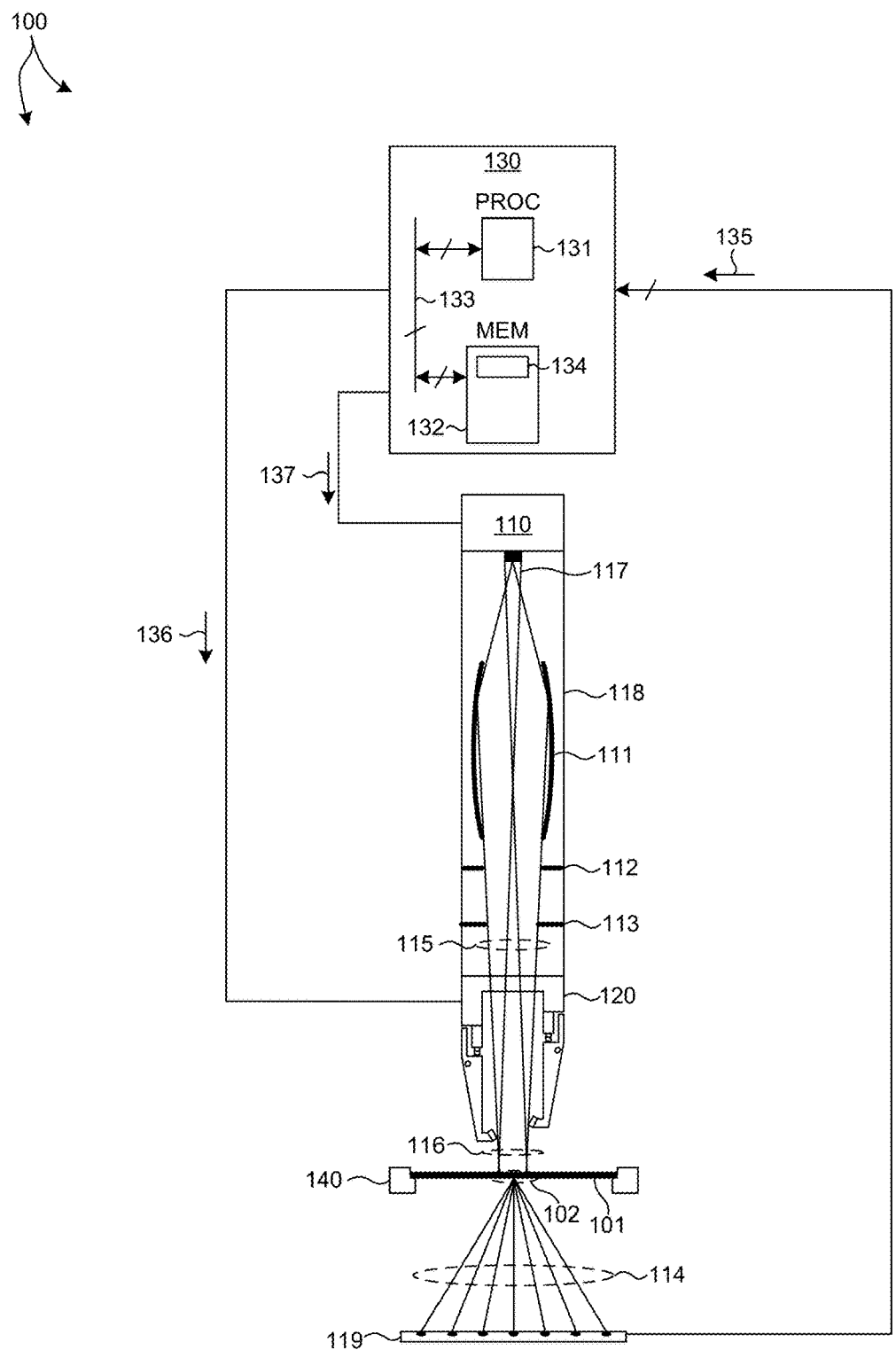
FIG. 1 is a diagram illustrative of a metrology system 100 configured to perform calibration of various system parameters in accordance with the methods described herein.

FIG. 1 illustrates an embodiment of a T-SAXS metrology tool 100 for measuring characteristics of a specimen in accordance with the exemplary methods presented herein. As shown in FIG. 1, the system 100 may be used to perform T-SAXS measurements over an inspection area 102 of a specimen 101 illuminated by an illumination beam spot.

In the depicted embodiment, metrology tool 100 includes an x-ray illumination source 110 configured to generate x-ray radiation suitable for T-SAXS measurements. In some embodiments, the x-ray illumination source 110 is configured to generate wavelengths between 0.01 nanometers and 1 nanometer. In general, any suitable high-brightness x-ray illumination source capable of generating high brightness x-rays at flux levels sufficient to enable high-throughput, inline metrology may be contemplated to supply x-ray illumination for T-SAXS measurements. In some embodiments, an x-ray source includes a tunable monochromator that enables the x-ray source to deliver x-ray radiation at different, selectable wavelengths.

In some embodiments, one or more x-ray sources emitting radiation with photon energy greater than 15 keV are employed to ensure that the x-ray source supplies light at wavelengths that allow sufficient transmission through the entire device as well as the wafer substrate. By way of non-limiting example, any of a particle accelerator source, a liquid anode source, a rotating anode source, a stationary, solid anode source, a microfocus source, a microfocus rotating anode source, a plasma based source, and an inverse Compton source may be employed as x-ray illumination source 110. In one example, an inverse Compton source available from Lyncean Technologies, Inc., Palo Alto, Calif. (USA) may be contemplated. Inverse Compton sources have an additional advantage of being able to produce x-rays over a range of photon energies, thereby enabling the x-ray source to deliver x-ray radiation at different, selectable wavelengths.

Exemplary x-ray sources include electron beam sources configured to bombard solid or liquid targets to stimulate x-ray radiation. Methods and systems for generating high brightness, liquid metal x-ray illumination are described in U.S. Pat. No. 7,929,667, issued on Apr. 19, 2011, to KLA-Tencor Corp., the entirety of which is incorporated herein by reference.

X-ray illumination source 110 produces x-ray emission over a source area having finite lateral dimensions (i.e., non-zero dimensions orthogonal to the beam axis. Focusing optics 111 focuses source radiation onto a metrology target located on specimen 101. The finite lateral source dimension results in finite spot size 102 on the target defined by the rays 117 coming from the edges of the source. In some embodiments, focusing optics 111 includes elliptically shaped focusing optical elements.

A beam divergence control slit 112 is located in the beam path between focusing optics 111 and beam shaping slit mechanism 120. Beam divergence control slit 112 limits the divergence of the illumination provided to the specimen under measurement. An additional intermediate slit 113 is located in the beam path between beam divergence control slit 112 and beam shaping slit mechanism 120. Intermediate slit 113 provides additional beam shaping. In general, however, intermediate slit 113 is optional.

Beam shaping slit mechanism 120 is located in the beam path immediately before specimen 101. In one aspect, the slits of beam shaping slit mechanism 120 are located in close proximity to specimen 101 to minimize the enlargement of the incident beam spot size due to beam divergence defined by finite source size. In one example, expansion of the beam spot size due to shadow created by finite source size is approximately one micrometer for a 10 micrometer x-ray source size and a distance of 25 millimeters between the beam shaping slits and specimen 101.

In some embodiments, beam shaping slit mechanism 120 includes multiple, independently actuated beam shaping slits (i.e., blades). In one embodiment, beam shaping slit mechanism 120 includes four independently actuated beam shaping slits. These four beams shaping slits effectively block a portion of incoming beam 115 and generate an illumination beam 116 having a box shaped illumination cross-section.

Figure 2:
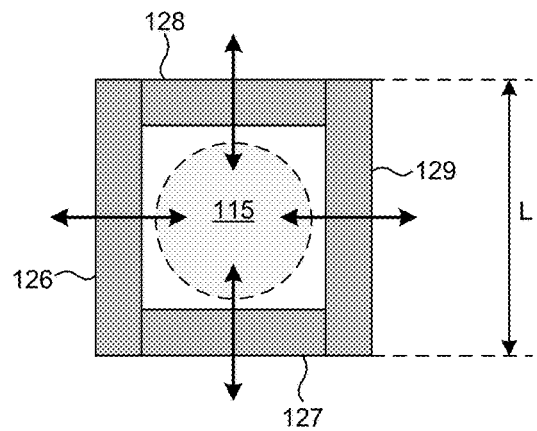
FIG. 2 depicts a end view of beam shaping slit mechanism 120 in one configuration.
Figure 3:
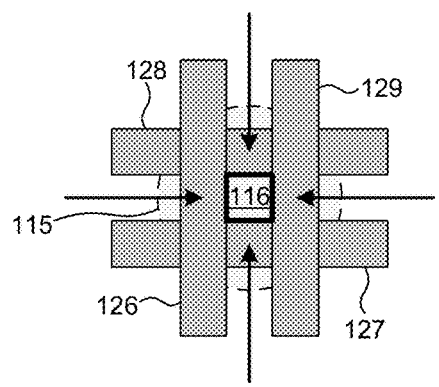
FIG. 3 depicts a end view of beam shaping slit mechanism 120 in another configuration.

FIGS. 2 and 3 depict an end view of beam shaping slit mechanism 120 depicted in FIG. 1 in two different configurations. As illustrated in FIGS. 2 and 3, the beam axis is perpendicular to the drawing page. As depicted in FIG. 2, incoming beam 115 has a large cross-section. In some embodiments, incoming beam 115 has a diameter of approximately one millimeter. Furthermore, the location of incoming beam 115 within beam shaping slits 126-129 may have an uncertainty of approximately three millimeters due to beam pointing errors. To accommodate the size of the incoming beam and the uncertainty of the beam location, each slit has a length, L, of approximately six millimeters. As depicted in FIG. 2, each slit is moveable in a direction perpendicular to the beam axis. In the illustration of FIG. 2, slits 126-129 are located at a maximum distance from the beam axis (i.e., the slits are fully open and they are not restricting the light passing through beam shaping slit mechanism 120.

FIG. 3 depicts slits 126-129 of beam shaping slit mechanism 120 in positions that block a portion of incoming beam 115, such that outgoing beam 116 delivered to the specimen under measurement has reduced size and well-defined shape. As depicted in FIG. 3, each of slits 126-129 has moved inward, toward the beam axis to achieve the desired output beam shape.

Slits 126-129 are constructed from materials that minimize scattering and effectively block incident radiation. Exemplary materials include single crystal materials such as Germanium, Gallium Arsenide, Indium Phosphide, etc. Typically, the slit material is cleaved along a crystallographic direction, rather than sawn, to minimize scattering across structural boundaries. In addition, the slit is oriented with respect to the incoming beam such that the interaction between the incoming radiation and the internal structure of the slit material produces a minimum amount of scattering. The crystals are attached to each slit holder made of high density material (e.g., tungsten) for complete blocking of the x-ray beam on one side of the slit. In some embodiments, each slit has a rectangular cross-section having a width is approximately 0.5 millimeters and a height of approximately 1-2 millimeters. As depicted in FIG. 2, the length, L, of a slit is approximately 6 millimeters.

In general, x-ray optics shape and direct x-ray radiation to specimen 101. In some examples, the x-ray optics include an x-ray monochromator to monochromatize the x-ray beam that is incident on the specimen 101. In some examples, the x-ray optics collimate or focus the x-ray beam onto measurement area 102 of specimen 101 to less than 1 milliradian divergence using multilayer x-ray optics. In these examples, the multilayer x-ray optics function as a beam monochromator, also. In some embodiments, the x-ray optics include one or more x-ray collimating mirrors, x-ray apertures, x-ray beam stops, refractive x-ray optics, diffractive optics such as zone plates, Montel optics, specular x-ray optics such as grazing incidence ellipsoidal mirrors, polycapillary optics such as hollow capillary x-ray waveguides, multilayer optics or systems, or any combination thereof. Further details are described in U.S. Patent Publication No. 2015/0110249, the content of which is incorporated herein by reference it its entirety.

X-ray detector 119 collects x-ray radiation 114 scattered from specimen 101 and generates an output signals 135 indicative of properties of specimen 101 that are sensitive to the incident x-ray radiation in accordance with a T-SAXS measurement modality. In some embodiments, scattered x-rays 114 are collected by x-ray detector 119 while specimen positioning system 140 locates and orients specimen 101 to produce angularly resolved scattered x-rays.

In some embodiments, a T-SAXS system includes one or more photon counting detectors with high dynamic range (e.g., greater than $10^5$). In some embodiments, a single photon counting detector detects the position and number of detected photons.

In some embodiments, the x-ray detector resolves one or more x-ray photon energies and produces signals for each x-ray energy component indicative of properties of the specimen. In some embodiments, the x-ray detector 119 includes any of a CCD array, a microchannel plate, a photodiode array, a microstrip proportional counter, a gas filled proportional counter, a scintillator, or a fluorescent material.

In this manner the X-ray photon interactions within the detector are discriminated by energy in addition to pixel location and number of counts. In some embodiments, the X-ray photon interactions are discriminated by comparing the energy of the X-ray photon interaction with a predetermined upper threshold value and a predetermined lower threshold value. In one embodiment, this information is communicated to computing system 130 via output signals 135 for further processing and storage.

In a further aspect, a T-SAXS system is employed to determine properties of a specimen (e.g., structural parameter values) based on one or more diffraction orders of scattered light. As depicted in FIG. 1, metrology tool 100 includes a computing system 130 employed to acquire signals 135 generated by detector 119 and determine properties of the specimen based at least in part on the acquired signals.

In some examples, metrology based on T-SAXS involves determining the dimensions of the sample by the inverse solution of a pre-determined measurement model with the measured data. The measurement model includes a few (on the order of ten) adjustable parameters and is representative of the geometry and optical properties of the specimen and the optical properties of the measurement system. The method of inverse solve includes, but is not limited to, model based regression, tomography, machine learning, or any combination thereof. In this manner, target profile parameters are estimated by solving for values of a parameterized measurement model that minimize errors between the measured scattered x-ray intensities and modeled results.

It is desirable to perform measurements at large ranges of angle of incidence and azimuth angle to increase the precision and accuracy of measured parameter values. This approach reduces correlations among parameters by extending the number and diversity of data sets available for analysis to include a variety of large-angle, out of plane orientations. For example, in a normal orientation, T-SAXS is able to resolve the critical dimension of a feature, but is largely insensitive to sidewall angle and height of a feature. However, by collecting measurement data over a broad range of out of plane angular orientations, the sidewall angle and height of a feature can be resolved. In other examples, measurements performed at large ranges of angle of incidence and azimuth angle provide sufficient resolution and depth of penetration to characterize high aspect ratio structures through their entire depth.

Measurements of the intensity of diffracted radiation as a function of x-ray incidence angle relative to the wafer surface normal are collected. Information contained in the multiple diffraction orders is typically unique between each model parameter under consideration. Thus, x-ray scattering yields estimation results for values of parameters of interest with small errors and reduced parameter correlation.

Figure 4:
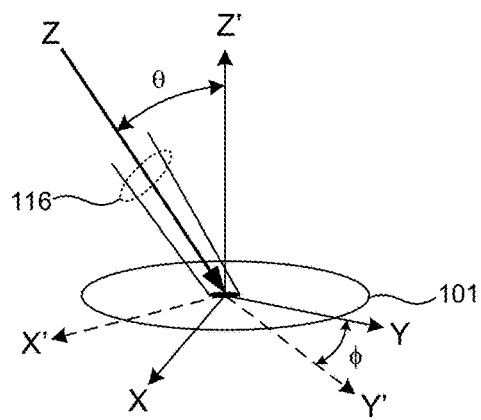
FIG. 4 depicts x-ray illumination beam 116 incident on wafer 101 at a particular orientation described by angles ϕ and θ.

Each orientation of the illuminating x-ray beam 116 relative to the surface normal of a semiconductor wafer 101 is described by any two angular rotations of wafer 101 with respect to the x-ray illumination beam 115, or vice-versa. In one example, the orientation can be described with respect to a coordinate system fixed to the wafer. FIG. 4 depicts x-ray illumination beam 116 incident on wafer 101 at a particular orientation described by an angle of incidence, $\theta$, and an azimuth angle, $\phi$. Coordinate frame XYZ is fixed to the metrology system (e.g., illumination beam 116) and coordinate frame X'Y'Z' is fixed to wafer 101. The Y axis is aligned in plane with the surface of wafer 101. X and Z are not aligned with the surface of wafer 101. Z' is aligned with an axis normal to the surface of wafer 101, and X' and Y' are in a plane aligned with the surface of wafer 101. As depicted in FIG. 4, x-ray illumination beam 116 is aligned with the Z-axis and thus lies within the XZ plane. Angle of incidence, $\theta$, describes the orientation of the x-ray illumination beam 116 with respect to the surface normal of the wafer in the XZ plane. Furthermore, azimuth angle, $\phi$, describes the orientation of the XZ plane with respect to the X'Z' plane. Together, $\theta$ and $\phi$, uniquely define the orientation of the x-ray illumination beam 116 with respect to the surface of wafer 101. In this example, the orientation of the x-ray illumination beam with respect to the surface of wafer 101 is described by a rotation about an axis normal to the surface of wafer 101 (i.e., Z' axis) and a rotation about an axis aligned with the surface of wafer 101 (i.e., Y axis). In some other examples, the orientation of the x-ray illumination beam with respect to the surface of wafer 101 is described by a rotation about a first axis aligned with the surface of wafer 101 and another axis aligned with the surface of wafer 101 and perpendicular to the first axis.

As illustrated in FIG. 1, metrology tool 100 includes a specimen positioning system 140 configured to both align specimen 101 and orient specimen 101 over a large range of angles of incidence and azimuth angle with respect the illumination beam 116. In some embodiments, specimen positioning system 140 is configured to rotate specimen 101 over a large range of angles of rotation (e.g., at least 60 degrees) aligned in-plane with the surface of specimen 101. In this manner, angle resolved measurements of specimen 101 are collected by metrology system 100 over any number of locations and orientations on the surface of specimen 101. In one example, computing system 130 communicates command signals (not shown) to specimen positioning system 140 that indicate the desired position of specimen 101. In response, specimen positioning system 140 generates command signals to the various actuators of specimen positioning system 140 to achieve the desired positioning of specimen 101.

Figure 5:
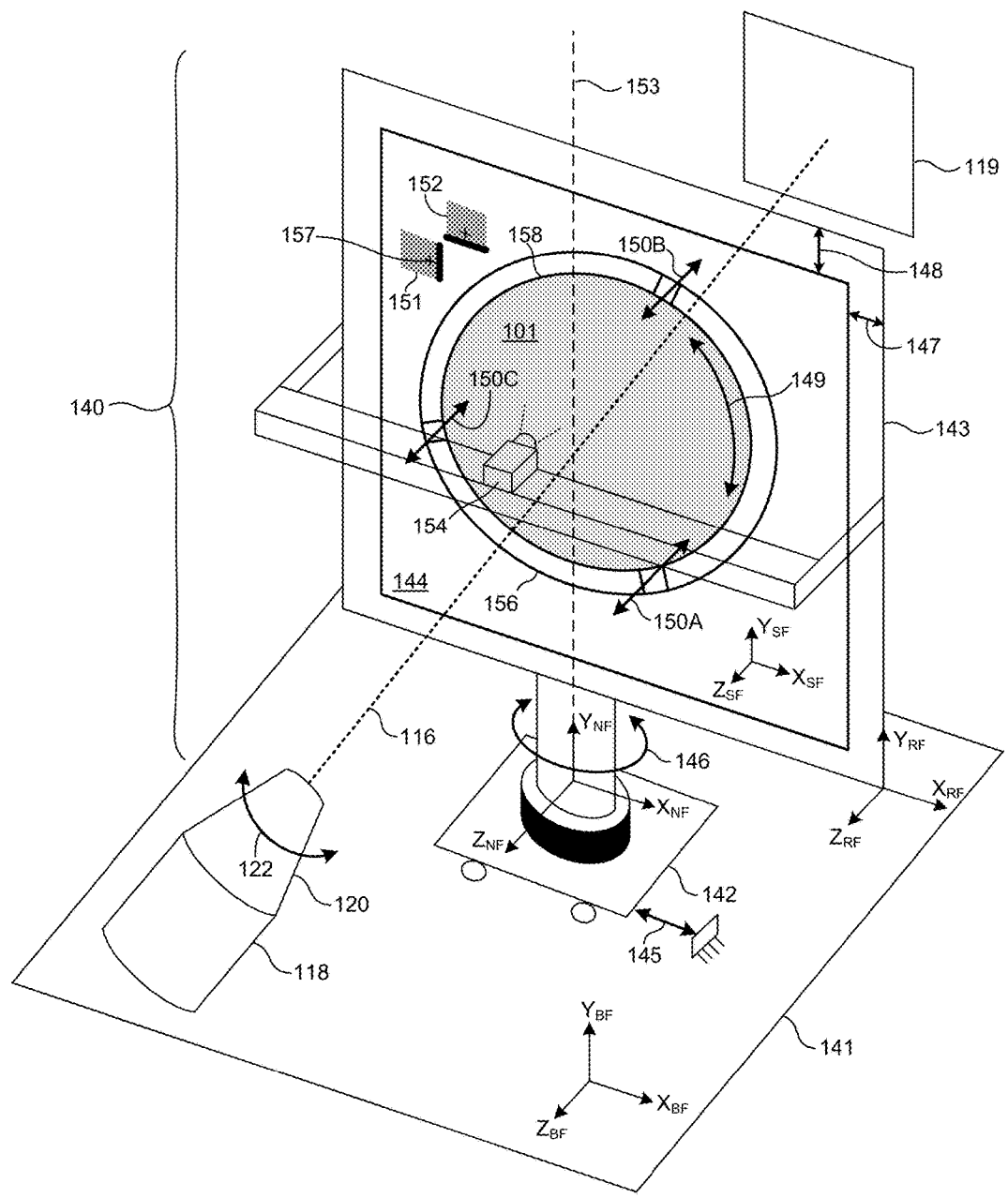
FIG. 5 is a diagram illustrative of a specimen positioning system 140 with the wafer stage moved to a position where the illumination beam 116 is incident on wafer 101.

FIG. 5 depicts a specimen positioning system 140 in one embodiment. As depicted in FIG. 5, specimen positioning system 140 includes a base frame 141, a lateral alignment stage 142, a stage reference frame 143, and a wafer stage 144. For reference purposes, the $\{X_{BF}, Y_{BF}, Z_{BF}\}$ coordinate frame is attached to base frame 141, the $\{X_{NF}, Y_{NF}, Z_{NF}\}$ coordinate frame is attached to lateral alignment stage 142, the $\{X_{RF}, Y_{RF}, Z_{RF}\}$ coordinate frame is attached to stage reference frame 143, and the $\{X_{SF}, Y_{SF}, Z_{SF}\}$ coordinate frame is attached to wafer stage 144. Wafer 101 is supported on wafer stage 144 by a tip-tilt-Z stage 156 including actuators 150A-C. A rotary stage 158 mounted to tip-tilt-Z stage 156 orients wafer 101 over a range of azimuth angles, $\phi$, with respect to illumination beam 116. In the depicted embodiment, three linear actuators 150A-C are mounted to the wafer stage 144 and support rotary stage 158, which, in turn, supports wafer 101.

Actuator 145 translates the lateral alignment stage 142 with respect to the base frame 141 along the $X_{BF}$ axis. Rotary actuator 146 rotates the stage reference frame 143 with respect to lateral alignment stage 142 about an axis of rotation 153 aligned with the $Y_{NF}$ axis. Rotary actuator 146 orients wafer 101 over a range of angles of incidence, θ, with respect to illumination beam 116. Wafer stage actuators 147 and 148 translate the wafer stage 144 with respect to the stage reference frame 143 along the $X_{RF}$ and $Y_{RF}$ axes, respectively. Actuators 150A-C operate in coordination to translate the rotary stage 158 and wafer 101 with respect to the wafer stage 144 in the $Z_{SF}$ direction and tip and tilt rotary stage 158 and wafer 101 with respect to the wafer stage 144 about axes coplanar with the $X_{SF}$-$Y_{SF}$ PLANE. ROTARY STAGE 158 ROTATES WAFER 101 ABOUT AN axis normal to the surface of wafer 101.

In summary, wafer stage 144 is capable of moving the wafer 101 with respect to the illumination beam 116 such that illumination beam 116 may be incident at any location on the surface of wafer 101 (i.e., at least 300 millimeter range in XRF and YRF directions). Rotary actuator 146 is capable of rotating the stage reference frame 143 with respect to the illumination beam 116 such that illumination beam 116 may be incident at the surface of wafer 101 at any of a large range of angles of incidence (e.g., greater than two degrees). In one embodiment, rotary actuator 146 is configured to rotate stage reference frame 143 over a range of at least sixty degrees. Rotary stage 158 mounted to wafer stage 144 is capable of rotating the wafer 101 with respect to the illumination beam 116 such that illumination beam 116 may be incident at the surface of wafer 101 at any of a large range of azimuth angles (e.g., at least ninety degrees rotational range).

In some other embodiments, lateral alignment stage 142 is removed and stage reference frame 143 is rotated with respect to base frame 141 by rotary actuator 146. In these embodiments, the x-ray illumination system includes one or more actuators that move one or more optical elements of the x-ray illumination system that cause the x-ray illumination beam 116 to move with respect to the base frame 141, for example, in the $X_{BF}$ direction. In these embodiments, movements of stage reference stage 143 for purposes of calibration as described herein are replaced by movements of one or more optical elements of the x-ray illumination system move the x-ray illumination beam to the desired position with respect to the axis of rotation 153, for example.

In some embodiments, such as the embodiment depicted in FIG. 5, a specimen positioning system includes at least one beam occlusion element and an alignment camera employed to calibrate the location of incidence of the illumination beam and align the axis of rotation of the stage reference frame with respect to the illumination beam at the point of incidence of illumination beam with a wafer. The occlusion element(s) is mounted to the wafer stage coplanar with the surface of the wafer under measurement. The alignment camera is mounted to the stage reference frame, and thus rotates with the stage reference frame.

In the embodiment depicted in FIG. 5, the occlusion elements are cylindrical pin shaped elements 151 and 152 mounted to wafer stage 144 such that the central axis of the cylindrical pin shaped elements 151 and 152 are approximately co-planar with the surface of wafer 101. As depicted in FIG. 5, cylindrical pin element 151 includes a central axis approximately aligned parallel with the $Y_{NF}$ axis and cylindrical pin element 152 includes a central axis approximately aligned parallel with the $X_{RF}$ axis. Similar to a beam slit, the cylindrical pin occludes the beam by absorption of a large fraction of any impinging x-rays.

Specimen positioning system 140 also includes an alignment camera 154 mounted to stage reference frame 143. Alignment camera 154 is configured to generate high resolution images of objects in its field of view, such as wafer 101. Alignment camera 154 also includes an auto-focus mechanism that maintains a sharp image focus by precisely moving the focal point of the camera by a measured distance. In this manner, alignment camera 154 can be used to measure relative distances between the stage reference frame to which the camera body is mounted and wafer 101 or cylindrical pin elements 151 and 152 imaged by the camera by monitoring the z-displacement of the focal point of the camera.

In one aspect, the precise location of incidence of the illumination beam in two dimensions in the plane of the surface of the wafer is determined based on the interaction of the illumination beam with two or more occlusion elements.

Figure 7:
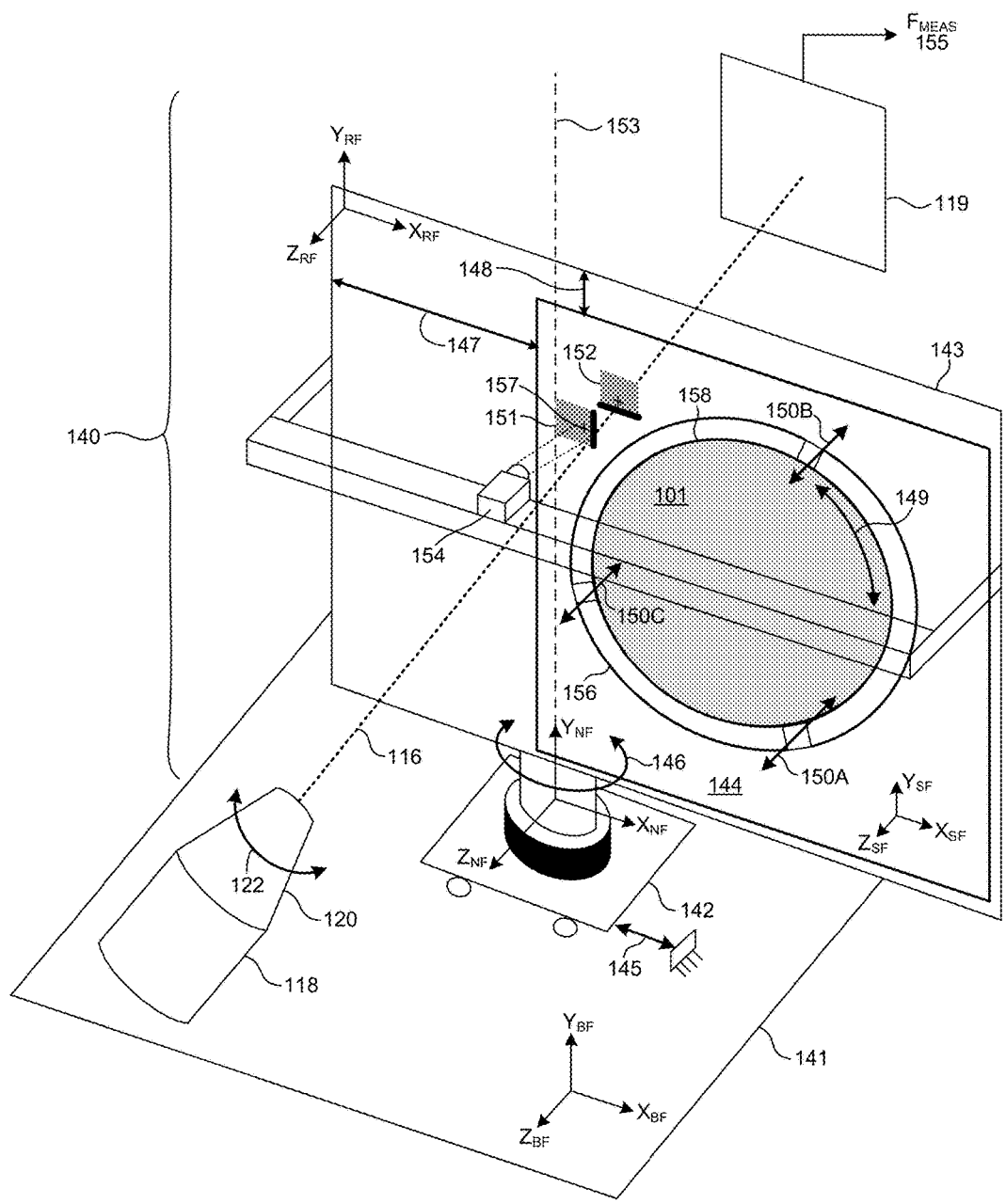
FIG. 7 is a diagram illustrative of the specimen positioning system 140 with the wafer stage moved to a position where the illumination beam 116 is occluded by a cylindrical pin element 151.

FIG. 7 is a diagram illustrative of the specimen positioning system 140 with the wafer stage moved to a position where the illumination beam 116 is occluded by the cylindrical pin element 151. The precise location of incidence of the illumination beam with respect to cylindrical pin 151 is determined based on transmitted flux measured by detector 119 as a function of the X position of cylindrical pin 151 with respect to illumination beam 116 (i.e., base frame 141). As depicted in FIG. 7, as cylindrical pin 151 is moved in the positive X-direction (in the direction of $X_{BF}$), more and more of illumination beam 116 is occluded by cylindrical pin 151. As a result fewer photons reach detector 119. However, as cylindrical pin 151 is moved in the negative X-direction (opposite $X_{BF}$), less and less of illumination beam 116 is occluded by cylindrical pin 151. Detector 119 generates signals 155 indicative of the measured flux as a function of X-position and the results are analyzed to identify the position of the cylindrical pin that corresponds with the center of illumination beam 116.

Figure 8:
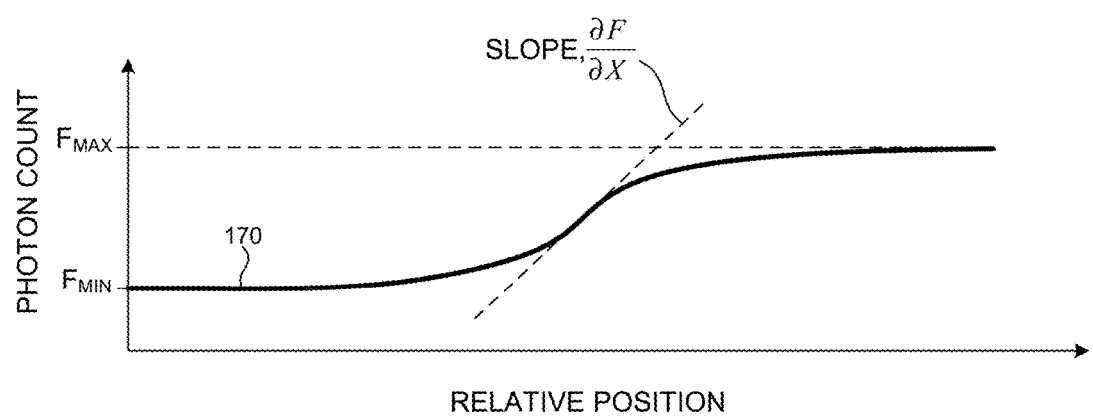
FIG. 8 depicts a plot 170 illustrative of measured flux as a function of relative position of an occlusion element with respect to illumination beam 116.

FIG. 8 depicts a plot 170 illustrative of measured flux as a function of relative position of a cylindrical pin or, alternatively, a knife edge, with respect to illumination beam 116. The depicted relationship between measured flux 155 and relative position is a sigmoid function.

In some examples, the beam center is determined to be the relative position of the cylindrical pin with respect to the illumination beam where the measured flux is halfway between the minimum flux value, $F_{MIN}$, and the maximum flux value, $F_{MAX}$. However, in some other examples, the beam center may be determined at another flux value different from the middle of the range of measured flux. In some examples, a more precise relationship is determined by modeling of the interaction of the beam with the material and geometry of the cylindrical pin or knife edge. In these examples, the modelled interaction is compared with the measured transmitted flux, and a fitting algorithm is used to determine the relative position of the cylindrical pin or knife edge with respect to the illumination beam that aligns with the beam center based on the fit of the measured results to the model.

In one example, an estimate of the distance, ΔX, between a current position of cylindrical pin 151 with respect to the center of illumination beam 116 and a position of the cylindrical pin 151 that coincides with the beam center is based on the measured flux, $F_{MEAS}$, the mid-point of the flux, $F_{MID}$, and the inverse of the derivative of the measured flux as a function of cylindrical pin position as described by equation (1)

$$\Delta X = \frac{\partial X}{\partial F}(F_{MEAS} - F_{MID}) \quad (1)$$

and $F_{MID}$ is described by equation (2).

$$F_{MID} = \frac{F_{MIN} + F_{MAX}}{2} \quad (2)$$

The maximum and minimum values of measured flux can be measured by scanning the wafer stage while measuring transmitted flux. Furthermore, the slope at the mid-point can also be estimated. Based on these quantities, an estimate of the change in centered position of the cylindrical pin is determined in accordance with equation (1) simply by measuring flux at one position. If necessary, the change in centered position can be determined iteratively to converge on a centered position.

Since the beam has a centroid component in two directions (e.g., X and Y directions), two cylindrical pins each oriented perpendicular to the direction of the centroid component are measured. In the embodiment depicted in FIG. 7, cylindrical pin 151 is employed to locate the beam center with respect to the stage reference frame in the X-direction and cylindrical pin 152 is employed to locate the beam center with respect to the stage reference frame in the Y-direction. In general, more than two cylindrical pins may be utilized to generate redundancy and increase the accuracy of the calibration of the beam location.

In a further aspect, the position of incidence of the illumination beam is determined at any location on the wafer based on images measured by an alignment camera. As depicted in FIG. 7, the center of the illumination beam 116 is aligned with the vertically and horizontally oriented cylindrical pins 151 and 152 as described hereinbefore. In the embodiment depicted in FIG. 7, a fiducial mark 157 is located co-planar with the central axis of cylindrical pin 151. Similarly, a fiducial mark is located co-planar with the central axis of cylindrical pin 152. At the location of beam center alignment with cylindrical pin 151, the position of the illumination beam 116 with respect to cylindrical pin 151, or fiducial 157 at or near the cylindrical pin, is recorded by alignment camera 154. This registers the relative position of the illumination beam with respect to a precise location in the field of view of the alignment camera (assuming no change in focus position). As depicted in FIG. 5, wafer 101 is moved within the field of view of alignment camera 154. Wafer 101 is moved such that a desired location (e.g., a fiducial mark) on the wafer is imaged within the field of view of alignment camera 154. The position of the illumination beam 116 with respect to the desired location is determined by alignment camera 154 based on the previous registration. In this manner, the position of the illumination beam 116 on wafer 101 in the X and Y direction is quickly estimated based on an image collected by the alignment camera 154. Similarly, the position of the wafer in the Z-direction with respect to the Z-location of cylindrical pin 151 is measured by changing the focus position of alignment camera 154 until the lithographic features on the surface of wafer 101 come into precise focus. The change i-sin focus position is indicative of the difference in Z-position between the cylindrical pin and the imaged location on the wafer. Actuators 150A-C may be employed to reposition wafer 101 in the Z-direction to relocate the imaged location to be in plane with the cylindrical pin (e.g. fiducial 157).

In a further aspect, the position of incidence of the illumination beam is determined at any location on the wafer based on wafer stage coordinates. Once the center of the illumination beam is aligned with the vertical and horizontal cylindrical pins, and the position of the illumination beam with respect to the cylindrical pin, or a fiducial mark at or near the knife edge, is recorded by an alignment camera as described hereinbefore, the location of incidence of the illumination beam can be transferred to stage coordinates. As depicted in FIG. 5, wafer 101 is moved within the field of view of alignment camera 154. The movement of wafer 101 is measured by the position measurement system of wafer stage 144 (e.g., linear encoders, etc.) By moving wafer 101 to three or more desired locations (e.g., a fiducial mark) on the wafer imaged within the field of view of alignment camera 154, the position of the illumination beam with respect to the desired location is determined at each desired location, along with the position of the wafer in stage coordinates. Based on the known location of the illumination beam and stage coordinates at the three or more locations, a map is generated that relates stage coordinates to the location of incidence of the illumination beam.

After locating the cylindrical pin 151 at the center of illumination beam 116 (in the X-direction), alignment camera 154 images the location of the cylindrical pin itself, or a fiducial mark located on or near the cylindrical pin, to establish a relationship between beam location and image location within the field of view of alignment camera 154. Since alignment camera 154 is located in a fixed, or repeatable, position with respect to the stage reference frame 143, the image registers the location of the illumination beam with respect to the stage reference frame 143, and thus serves as a reference for beam location in the X-direction. Moreover, alignment camera 154 establishes a precise focus position of the cylindrical pin itself, or a fiducial mark, to establish a precise Z-location of the cylindrical pin with respect to stage reference frame 143. Since the alignment camera 154 rotates with the stage reference frame, the focus position of the alignment camera 154 serves as a reference for Z-position of the cylindrical pin with respect to the stage reference frame.

In some embodiments, an occlusion element is a knife edge structure. A knife edge structure is typically a thin, sharpened dense high-Z material such as tungsten carbide, with a straight edge that is oriented perpendicular to the direction of position to be calibrated. In addition, the edge of the knife edge is coincident with the surface of the wafer. This enables the alignment camera 154 to focus on the same plane as the wafer, ensuring a good match between measured beam location at the wafer and the reference beam location at the knife edge as measured by the alignment camera.

In some embodiments, the occlusion element is a precision cylinder of known diameter as described hereinbefore. In these embodiments, the occlusion of the beam is offset in the Z-direction by the radius of the cylinder. In these embodiments, an additional surface coincident with the central axis of the cylinder and marked with a fiducial reference mark (e.g., fiducial 157) is advantageous to refer the camera frame to the axis and radius of the cylindrical occlusion element. In these embodiments, the central axis of the cylindrical occlusion element is coincident with the surface of the wafer, and oriented perpendicular to the direction of position to be calibrated as described hereinbefore.

In general, an occlusion element may be linearly extended shape. In some examples, an occlusion element has a polygonal cross-section extended along a central axis of the polygon. In some examples, an occlusion element includes one or more planar surfaces that extend in a direction parallel to a central axis of the occlusion element.

Since occluded flux is utilized to estimate the location of beam incidence, there is a risk that changes in flux in the illumination beam will be interpreted as a shift in position. In some embodiments, the flux of the illumination beam is measured immediately before, after, or simultaneously with the knife-edge measurements. Variations in illumination flux are compensated in analysis of the measured flux 155 to eliminate their influence on the measurement.

To ensure measurement integrity, the location of incidence of illumination beam 116 on the surface of wafer 101 should remain stationary during measurements over a large range of angles of incidence and azimuth angles. To achieve this objective, the axis of rotation 153 of stage reference frame 143 must be approximately co-planar with the surface of wafer 101 at the measurement location. Furthermore, the axis of rotation 153 must be aligned with the illumination beam 116 in the $X_{BF}$ direction such that the axis of rotation 153 intersects the illumination beam 116 at the point of incidence of illumination beam 116 with wafer 101 at the measurement location.

Figure 6A:
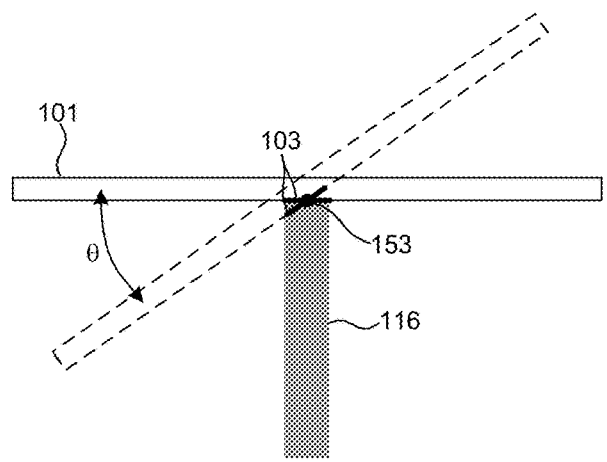
FIG. 6A depicts a top view of illumination beam 116 incident on wafer 101 as depicted in FIG. 5 where the rotational axis 153 intersects the illumination beam 116 at the point of incidence of illumination beam 116 with wafer 101.

FIG. 6A depicts a top view of illumination beam 116 incident on wafer 101 as depicted in FIG. 5. FIG. 6A depicts an end view of rotational axis 153 in a state of alignment where rotational axis 153 intersects the illumination beam 116 at the point of incidence of illumination beam 116 with wafer 101 at location 103 on wafer 101. As depicted in FIG. 6A, as wafer 101 is rotated about rotational axis 153 over a large angle of incidence, θ, illumination beam 116 remains incident at location 103. Thus, in this scenario, the location of incidence of illumination beam 116 on the surface of wafer 101 remains stationary during measurements over a large range of angles of incidence.

Figure 6B:
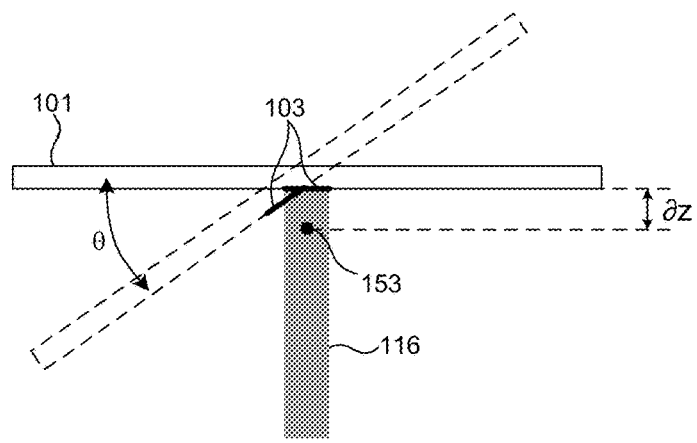
FIG. 6B depicts a top view of illumination beam 116 incident on wafer 101 as depicted in FIG. 5 where rotational axis 153 is misaligned with the surface of wafer 101 in the Z-direction.

FIG. 6B depicts a top view of illumination beam 116 incident on wafer 101 as depicted in FIG. 5. FIG. 6B depicts an end view of rotational axis 153 in a state of alignment where rotational axis 153 is misaligned with the surface of wafer 101 by a distance ∂z. As depicted in FIG. 6B, as wafer 101 is rotated about rotational axis 153 over a large angle of incidence, θ, a portion of location 103 is no longer illuminated (i.e., some other portion of wafer 101 is illuminated instead). Thus, in this scenario, the location of incidence of illumination beam 116 on the surface of wafer 101 drifts during measurements over a large range of angles of incidence, which is highly undesirable.

Figure 6C:
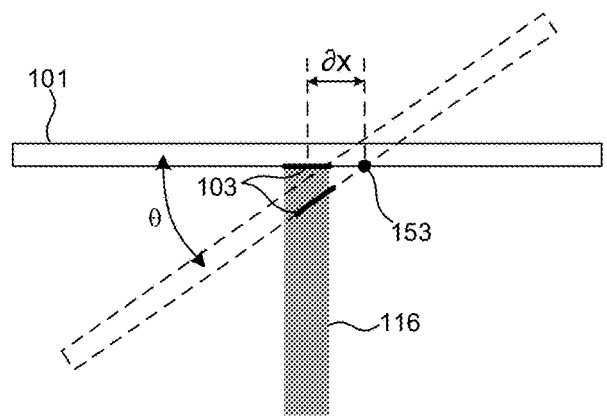
FIG. 6C depicts a top view of illumination beam 116 incident on wafer 101 as depicted in FIG. 5 where rotational axis 153 is offset from illumination beam 116 in the X-direction.

FIG. 6C depicts a top view of illumination beam 116 incident on wafer 101 as depicted in FIG. 5. FIG. 6C depicts an end view of rotational axis 153 in a state of alignment where rotational axis 153 is co-planar with the surface of wafer 101, but is offset from illumination beam 116 by a distance ∂x. As depicted in FIG. 6C, as wafer 101 is rotated about rotational axis 153 over a large angle of incidence, θ, a portion of location 103 is no longer illuminated (i.e., some other portion of wafer 101 is illuminated instead). Thus, in this scenario, the location of incidence of illumination beam 116 on the surface of wafer 101 drifts during measurements over a large range of angles of incidence, which is highly undesirable.

In another aspect, a specimen positioning system is calibrated to align the axis of rotation of the stage reference frame to be co-planar with the surface of the wafer, knife edges, or other occlusion elements and also align the axis of rotation of the stage reference frame with respect to the illumination beam in a direction approximately parallel to the surface of the wafer (e.g., the $X_{BF}$ direction) such that the axis of rotation and the illumination beam intersect at the point of incidence of illumination beam on the surface of wafer, knife edge, or other occlusion element.

In some embodiments, the calibration of the axis of rotation of the stage reference frame is achieved by aligning the center of the illumination beam with the X-direction occluding element (e.g., cylindrical pin 151) and measuring flux at a plurality of different rotational positions of the stage reference frame, θ. The apparent motion of the cylindrical pin in the X-direction (ΔX) is determined based on the chosen occlusion model as described hereinbefore (e.g., the sigmoid function depicted in FIG. 8, or another model). In addition, the apparent motion of the cylindrical pin in the X-direction is a function of 1) the distance of the cylindrical pin from the axis of rotation in the x-direction, ∂x, and in the z-direction, ∂z, 2) the distance from the beam center and the axis of rotation 153 in the x-direction, ∂n, and 3) the rotation angle about the axis of rotation 153 of the stage reference frame, θ. The relationship is described in equation (3).

$$\Delta X = \partial x \cos\theta + \partial z \sin\theta + \partial n \tag{3}$$

In one example, transmitted flux is measured at three angles of incidence, {−θ, 0, +Θ}. A linear system of equations described by equation (4) results from equation (3).

$$\begin{bmatrix} \Delta X_+ \\ \Delta X_0 \\ \Delta X_- \end{bmatrix} = \begin{bmatrix} 1 & \cos\Theta & \sin\Theta \\ 1 & 1 & 0 \\ 1 & \cos\Theta & -\sin\Theta \end{bmatrix} \begin{bmatrix} \partial n \\ \partial x \\ \partial z \end{bmatrix} = A_\Theta \begin{bmatrix} \partial n \\ \partial x \\ \partial z \end{bmatrix} \tag{4}$$

Equation (5) is obtained by inverting equation (4). Equation (5) solves for values of ∂n, ∂x, and ∂z from the apparent motion of the cylindrical pin in the X-direction.

$$\begin{bmatrix} \partial n \\ \partial x \\ \partial z \end{bmatrix} = \tag{5}$$

$$\frac{1}{2(\cos\Theta - 1)} \begin{bmatrix} -1 & 2\cos\Theta & -1 \\ 1 & -2 & 1 \\ \frac{(\cos\Theta - 1)}{\sin\Theta} & 0 & -\frac{(\cos\Theta - 1)}{\sin\Theta} \end{bmatrix} \begin{bmatrix} \Delta X_+ \\ \Delta X_0 \\ \Delta X_- \end{bmatrix} = A_\Theta^{-1} \Delta_X$$

Equation (5) combined with equation (2) solves for values of ∂n, ∂x, and ∂z from the apparent motion of the cylindrical pin in the X-direction determined from measured flux. In some examples, the solution for values of ∂n, ∂x, and ∂z is obtained iteratively as described by equation (6).

$$w_{k+1} = w_k + \frac{\partial X}{\partial F} A_\Theta^{-1} \begin{bmatrix} F_+ - F_{MID} \\ F_0 - F_{MID} \\ F_- - F_{MID} \end{bmatrix}, \tag{6}$$

where k is the iteration index and w is the vector [∂n, ∂x, and ∂z] of the values of the displacements of the actuators of specimen positioning system 140 required to align the axis of rotation 153 with the knife-edge 151 in the X and Z directions. The displacement, ∂n, is realized by actuator 145 moving the entire stage reference frame 143 with respect to the illumination beam 116 in the X-direction. The displacement, Ox, is realized by actuator 147 moving the cylindrical pin 151 back into alignment with the beam. The displacement, ∂z, is realized by actuators 150A-C moving the cylindrical pin in the Z-direction to align the axis of rotation 153 in plane with the central axis of the cylindrical pin in the Z-direction. Starting at an initial estimate, $w_0$, the recursion of equation (6) will converge to a point where the axis of rotation 153 is aligned to the cylindrical pin 151.

In general, equation (6) does not need to be applied exactly. The values of $A_\Theta$ and ∂x/∂F may be approximated numerically. In other examples, other matrices may be used, provided the iteration is stable and converges to the correct value.

In general, transmitted flux may be measured at any three or more different angles of incidence to determine values of displacements required to align the axis of rotation 153 with the knife-edge 151 in the X and Z directions. The selection of any three different angles of incidence results in a linear of system of equations that can be directly inverted. The selection of four efor more different angles of incidence results in an overdetermined linear system of equations that can be solved with a pseudoinverse algorithm to determine values of displacements required to align the axis of rotation 153 with the knife-edge 151 in the X and Z directions. The terms of the matrices illustrated in equations (4) and (5) depend on the selected angles of incidence. Thus, the terms will differ from equations (4) and (5) in examples where different angles of incidence are selected.

For purposes of alignment of the axis of rotation 153, a knife edge may be considered to be infinitesimally thin in the Z-direction with a vertical edge in the Y-direction. However, in practice, a knife edge does have a finite thickness. The additional absorption due to the longer path length at large angles of incidence may be modeled to compensate for this effect. In other embodiments where a cylindrical occlusion element is employed, the recursion described in equation (6) is applied, however, upon convergence, the radius, ρ, of the cylindrical occlusion element is subtracted from the offset in the X-direction to arrive at the correct alignment.

For an idealized beam occlusion element and axis of rotation, it would be sufficient to have only one beam occlusion element for beam calibration. Depending on the requirements of the system, however, multiple beam occlusion may be required. By aligning edges of multiple occlusion elements, it is possible to deduce any deviation of the axis of rotation from the nominal $Y_{NF}$ axis. Also, multiple identical occlusion elements allow the calibration of an edge from the right and the left, or up and down, helping eliminate systematic errors in the imaged edges (i.e., imaged by alignment camera 154) and the apparent edge deduced from the occluded flux change.

In some other embodiments, the calibration of the axis of rotation of the stage reference frame is achieved by locating a high-resolution x-ray camera having a focal plane aligned with the wafer plane of the wafer stage. The position of the illumination spot at the wafer plane is measured by the high resolution x-ray camera while the stage reference frame is rotated over a large range of angles of incidence. A mapping of the position of the illumination spot at the wafer plane as a function of the angle of incidence is generated based on the measurements. During measurements, the wafer stage is commanded to move in accordance with the mapping to maintain the same position of the illumination spot for all angles of incidence.

In some other embodiments, the calibration of the axis of rotation of the stage reference frame is achieved by locating a small target (i.e., on the order of the illumination spot size) on a wafer having a high diffraction efficiency. The strength of the diffracted orders is measured by detector 119 while the stage reference frame is rotated over a large range of angles of incidence. The strength of the diffracted orders is indicative of the misalignment between the illumination spot and the target as a function of angle of incidence. A mapping of the misalignment as a function of the angle of incidence is generated based on the measurements. During measurements, the wafer stage is commanded to move in accordance with the mapping to maintain the same position of the illumination spot for all angles of incidence.

In another aspect, a precise measurement of an AOI offset value between the normal (i.e., zero) angle of incidence of the illumination beam relative to the wafer surface and the zero angle of incidence as measured by the specimen positioning system (i.e., stage coordinates) is determined.

In some embodiments, the AOI offset value is determined based on absorption measurements over a range of AOIs. In one embodiment, an unpatterned area on wafer 101 is subjected to a scatterometry measurement by system 100 over a range of angles of incidence. The relative absorption of the wafer is determined based on the measured intensities of any or all of the diffraction orders as a function of the angle of incidence. Absorption follows Beer's exponential law, $\alpha = e^{-2\beta k_0 L}$, where L is the absorption length, β is the index of extinction of the material, and $k_0$ is the wavenumber. Furthermore, the absorption length is a geometric function of angle of incidence, $L = T \cos \theta$, where T is the thickness of the measured wafer. In some examples, a model of the expected response (e.g., Beer's law) is fit to the measured flux data to determine the offset between the AOI measured by stage metrology (e.g., a rotary encoder corresponding to actuator 146) and the measured AOI at detector 119. The offset is applied by stage positioning system 140 to correctly position wafer 101 at a desired measurement AOI based on stage metrology.

In some embodiments, the AOI offset value is determined based on measurements of diffraction orders scattered from a calibration grating at two azimuth angles separated by 180 degrees. FIG. 9A depicts a grating structure 171 measured by T-SAXS system 100 at an azimuth angle of zero. FIG. 9B depicts the same grating structure 171 measured by T-SAXS system 100 at an azimuth angle of 180 degrees. As illustrated in FIGS. 9A and 9B, the grating structure itself is tilted at an oblique angle □, with respect to the surface of the wafer. Although the illumination beam 116 is incident on the surface of the wafer at the same AOI for both azimuth angles, the illumination beam is incident on the tilted grating structures at different angles. Thus, by measuring the target at complimentary angles (i.e., azimuth angles separated by 180 degrees), the AOI offset induced by the specimen positioning system is maintained, while the AOI offset due to tilt of the grating structure is inverted.

FIG. 10 depicts a plot indicative of measured intensity of one diffraction order detected by detector 119 for a measurement 172 performed at a zero azimuth angle and another measurement 173 performed at an azimuth angle of 180 degrees. As depicted in FIG. 10, the symmetry point of measurements 172 and 173 indicates the AOI offset of the stage positioning system 140. The offset is applied by stage positioning system 140 to correctly position wafer 101 at a desired measurement AOI based on stage metrology.

In addition, the difference between the peak value of each scattering curve and the symmetry point is indicative of the tilt angle, α, associated with the measured structure. In this manner, calibration of an AOI offset is decoupled from an angular offset of the target structure itself by measuring one or more diffraction orders of a sample over a range of angles of incidence and two azimuth angles separated by 180 degrees.

In general, any combination of scattered orders could be used to separate angular offsets associated with tilt of the measured structure from angular offsets associated with the specimen positioning system. Utilizing more orders increases measurement accuracy and robustness.

This set of measurements provides an estimate of a value of a critical metrology parameter (e.g., etch hole tilt) without prior knowledge of the specific structure and is robust to systematic variation due to the differential nature of the measurement. Additional examples of robust and accurate x-ray based measurements are described in U.S. Patent Publication No. 2015/0117610 by Andrei Veldman, the contents of which are incorporated by reference herein in their entirety.

In another aspect, a precise measurement of an azimuth offset value between the zero azimuth angle of the wafer surface with respect to the illumination beam and the zero azimuth angle as measured by the specimen positioning system (i.e., stage coordinates) is determined. In addition, a precise measurement of an offset value between the center of the wafer surface and the center of rotation of rotary stage 158 is determined.

In some embodiments, alignment camera 154 captures images of known points (e.g., fiducials) located at different locations on wafer 101. Wafer 101 is moved by X actuator 147, Y actuator 148, and rotational actuator 149 to the different locations of the known points. From the images of the known points and the stage metrology coordinates associated with each of the images, a simple rigid body model is computed that determines the center point of rotation in wafer coordinates. In addition, an azimuth angle offset that characterizes the misalignment between zero azimuth in wafer coordinates and zero azimuth in stage coordinates is also determined based on the rigid body model. The azimuth angle offset is applied to rotary actuator 149 by stage positioning system 140 to correctly position wafer 101 at a desired azimuth angle based on stage metrology.

In some other embodiments, a low resolution camera estimates the center of rotation of images that have been rotated and translated by a known amount using well-known image registration techniques.

In another aspect, a precise calibration of the azimuth angle offset between wafer coordinates and stage coordinates is based on the position of the diffraction orders associated with measurements of a calibration grating at one or more azimuth angles. The calibration grating has a known grating direction. In one example, the diffraction pattern is measured by detector 119 for different azimuth angles. The azimuth angle is adjusted until the expected diffraction pattern is measured at detector 119. The azimuth angle associated with this measurement is the azimuth angle offset. If the detector is aligned with the stage, one incidence angle is sufficient to calibrate the azimuth angle of the wafer relative to the stage.

In another aspect, the detector is calibrated with respect to the stage and the azimuth angle is calibrated with respect to stage simultaneously using multiple, calibrated angles of incidence along with well-known formulae for conical diffraction. The detected diffraction orders move along a prescribed manifold as AOI is changed for a given azimuth angle at the stage. But, the rotational offset of the detector will appear as a constant offset.

In the depicted embodiments, beam shaping slit mechanism 120 is configured to rotate about the beam axis in coordination with the orientation of the specimen to optimize the profile of the incident beam for each angle of incidence, azimuth angle, or both. In this manner, the beam shape is matched to the shape of the metrology target. As depicted in FIG. 5, rotary actuator 122 rotates frame 120 and all attached mechanisms, actuators, sensors, and slits about the axis of illumination beam 116. Unfortunately, imperfections in rotary actuator 120 cause beam shaping slit mechanism 120 to precess about the axis of illumination beam 116 as the beam shaping slit mechanism 120 rotates with respect to flight tube 118. This causes the location of incidence of illumination beam 116 to drift for different azimuth angles and corresponding beam slit angles.

In a further aspect, a calibration map of X-Y stage offsets is determined based on measurements of the location of incidence of illumination beam 116 for a range of azimuth angles and corresponding beam slit angles.

In some embodiments, the measurements are performed by an x-ray camera having a focal plane at the location of the wafer surface. As the azimuth angle and corresponding beam slit angle is changed the location of incidence of illumination beam 116 is recorded. Based on the functional relationship between azimuth angle and incidence location, a calibration map is generated that provides X-Y stage offsets that maintain the same incidence location for any azimuth angle.

In some other embodiments, a calibration map of X-Y stage offsets is determined based on measurements of a small target (i.e., on the order of the illumination spot size) by detector 119 for a range of azimuth angles and corresponding beam slit angles. The target has high diffraction efficiency. The measured intensity of the diffraction orders is indicative of misalignment between the target and the location of incidence of illumination beam 116 for each azimuth angle and corresponding beam slit angle. Based on the functional relationship between azimuth angle and the measured misalignment, a calibration map is generated that provides X-Y stage offsets that maintain the same incidence location for any azimuth angle.

In another aspect, the shape of the surface of the wafer in the Z-direction is mapped using any of the alignment camera, an optical proximity sensor, a capacitive proximity sensor, or any other suitable proximity sensor. In some examples, the wafer surface is mapped on the front side (i.e., patterned side) of the wafer. In some other examples, the wafer surface is mapped on the back side of the wafer, provided the thickness of the wafer is sufficiently uniform or well modeled. In some examples, the wafer map is modeled using a number of standard interpolators (e.g., polynomial basis functions, rational functions, neural networks, etc.). Furthermore, it is possible to couple the lateral displacements and the height displacements using an analytical or numerical bending model of the wafer.

In a further aspect, the Z-actuators 150A-C are controlled to adjust the Z-position, Rx orientation, Ry orientation, or any combination thereof, in response to the shape of the surface of the wafer at the location of incidence of illumination beam 116. In one example, the tilt of the wafer is corrected by Z-actuators 150A-C. The tilt correction may be based on a map of wafer tilt or a value of tilt measured locally.

In another further aspect, the Z-actuators 150A-C are controlled to adjust the Z-position, Rx orientation, Ry orientation, or any combination thereof, to align the axis of rotation in azimuth with the stage reference frame 143. In one example, Z-actuators 150A-C are adjusted such that a specific target remains in focus of the alignment camera 154 over a range of azimuth angles. To perform this calibration, the wafer stage translates wafer 101 in the X and Y directions to maintain the target in the field of view of the alignment camera 154 for all azimuth angles.

In general, it is not possible to calibrate for all offset effects. Calibration to remove the largest deviation is typically chosen and remaining offsets are either ignored or handled by stage maps that account for non-idealities in the wafer and stage.

In addition, changes in temperature and air pressure or any other ambient condition may have an effect on the positioning of the illumination beam. In some embodiments, beam motion is correlated to these variables the position of the beam is adjusted based on measured temperature and pressure and the correlation model.

In general, specimen positioning system 140 may include any suitable combination of mechanical elements to achieve the desired linear and angular positioning performance, including, but not limited to goniometer stages, hexapod stages, angular stages, and linear stages.

In general, the focal plane of the illumination optics system is optimized for each measurement application. In this manner, system 100 is configured to locate the focal plane at various depths within the specimen depending on the measurement application. In one example, the specimen positioning system 140 is configured to move specimen 101 in the z-direction to locate the wafer within the focal plane of the optical system at the desired depth within specimen 101.

In some embodiments, x-ray illumination source 110, focusing optics 111, slits 112 and 113, or any combination thereof, are maintained in the same atmospheric environment as specimen 101 (e.g., gas purge environment). However, in some embodiments, the optical path length between and within any of these elements is long and X-ray scattering in air contributes noise to the image on the detector. Hence in some embodiments, any of x-ray illumination source 110, focusing optics 111, and slits 112 and 113 are maintained in a localized, vacuum environment separated from one another and the specimen (e.g., specimen 101) by vacuum windows.

Similarly, in some embodiments, x-ray detector 119 is maintained in the same atmospheric environment as specimen 101 (e.g., gas purge environment). However, in some embodiments, the distance between specimen 101 and x-ray detector 119 is lengthy and X-ray scattering in air contributes noise to the detected signals. Hence in some embodiments, one or more of the x-ray detectors is maintained in a localized, vacuum environment separated from the specimen (e.g., specimen 101) by a vacuum window.

Figure 11:
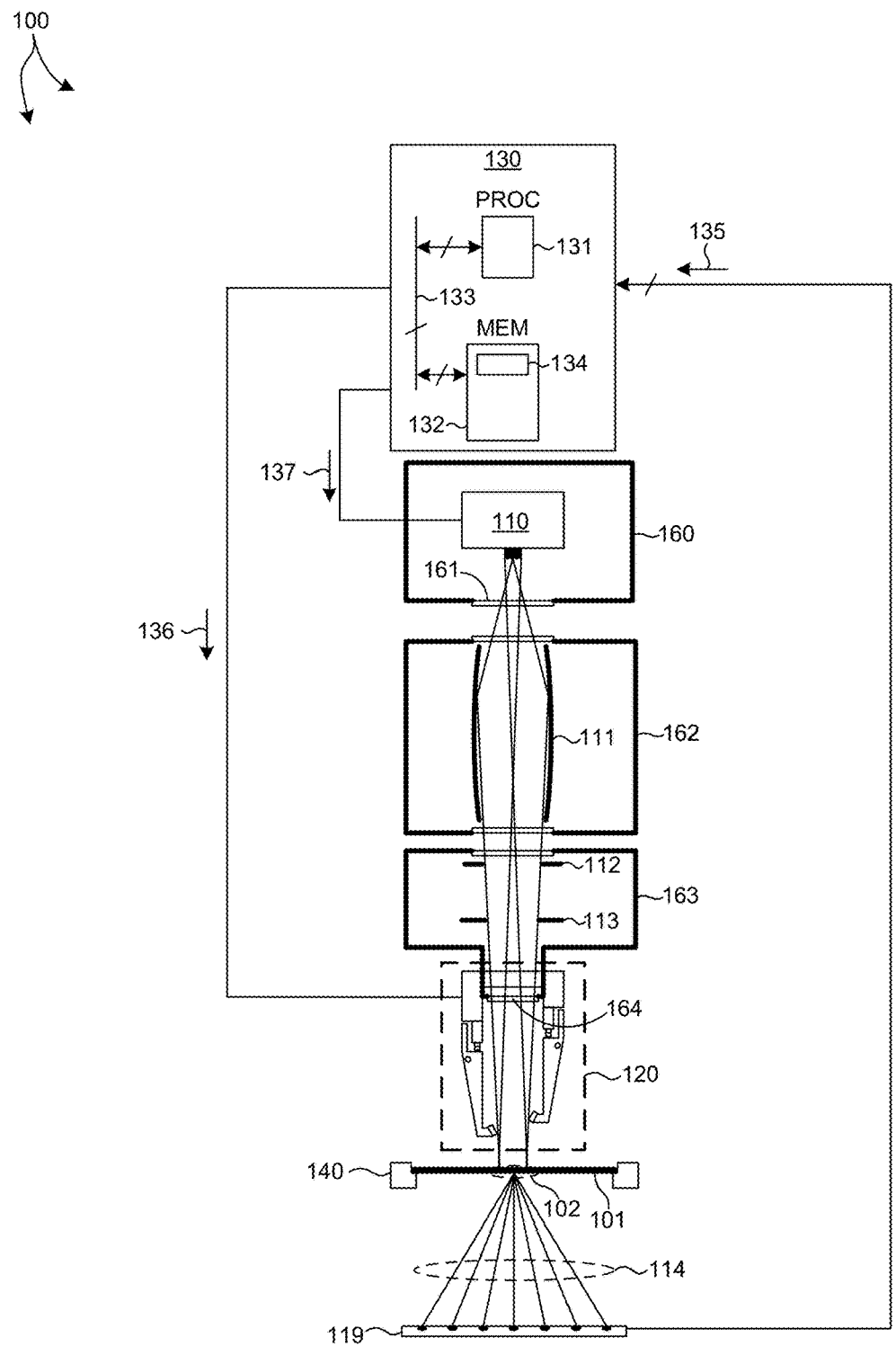
FIG. 11 is a diagram illustrative of elements of metrology system 100 contained in vacuum environments separate from specimen 101.

FIG. 11 is a diagram illustrative of a vacuum chamber 160 containing x-ray illumination source 110, vacuum chamber 162 containing focusing optics 111, and vacuum chamber 163 containing slits 112 and 113. The openings of each vacuum chamber are covered by vacuum windows. For example, the opening of vacuum chamber 160 is covered by vacuum window 161. Similarly, the opening of vacuum chamber 163 is covered by vacuum window 164. The vacuum windows may be constructed of any suitable material that is substantially transparent to x-ray radiation (e.g., Kapton, Beryllium, etc.). A suitable vacuum environment is maintained within each vacuum chamber to minimize scattering of the illumination beam. A suitable vacuum environment may include any suitable level of vacuum, any suitable purged environment including a gas with a small atomic number (e.g., helium), or any combination thereof. In this manner, as much of the beam path as possible is located in vacuum to maximize flux and minimize scattering.

In some embodiments, the entire optical system, including specimen 101, is maintained in vacuum. However, in general, the costs associated with maintaining specimen 101 in vacuum are high due to the complexities associated with the construction of specimen positioning system 140.

In another further aspect, beam shaping slit mechanism 120 is mechanically integrated with vacuum chamber 163 to minimize the beam path length subject to the atmospheric environment. In general, it is desirable to encapsulate as much of the beam as possible in vacuum before incidence with specimen 101. In some embodiments, the vacuum beam line extends into a hollow, cylindrically shaped cavity at the input of beam shaping slit mechanism 120. Vacuum window 164 is located at the output of vacuum chamber 163 within beam shaping slit mechanism 120 such that incoming beam 115 remains in vacuum within a portion of beam shaping slit mechanism 120, then passes through vacuum window 164 before interaction with any of slits 126-129 and specimen 101.

In the embodiment depicted in FIG. 1, focusing optics 111, slits 112 and 113, and beam shaping slit mechanism 120 are maintained in a controlled environment (e.g., vacuum) within a flight tube 118.

In another further aspect, computing system 130 is configured to generate a structural model (e.g., geometric model, material model, or combined geometric and material model) of a measured structure of a specimen, generate a T-SAXS response model that includes at least one geometric parameter from the structural model, and resolve at least one specimen parameter value by performing a fitting analysis of T-SAXS measurement data with the T-SAXS response model. The analysis engine is used to compare the simulated T-SAXS signals with measured data thereby allowing the determination of geometric as well as material properties such as electron density of the sample. In the embodiment depicted in FIG. 1, computing system 130 is configured as a model building and analysis engine configured to implement model building and analysis functionality as described herein.

Figure 12:
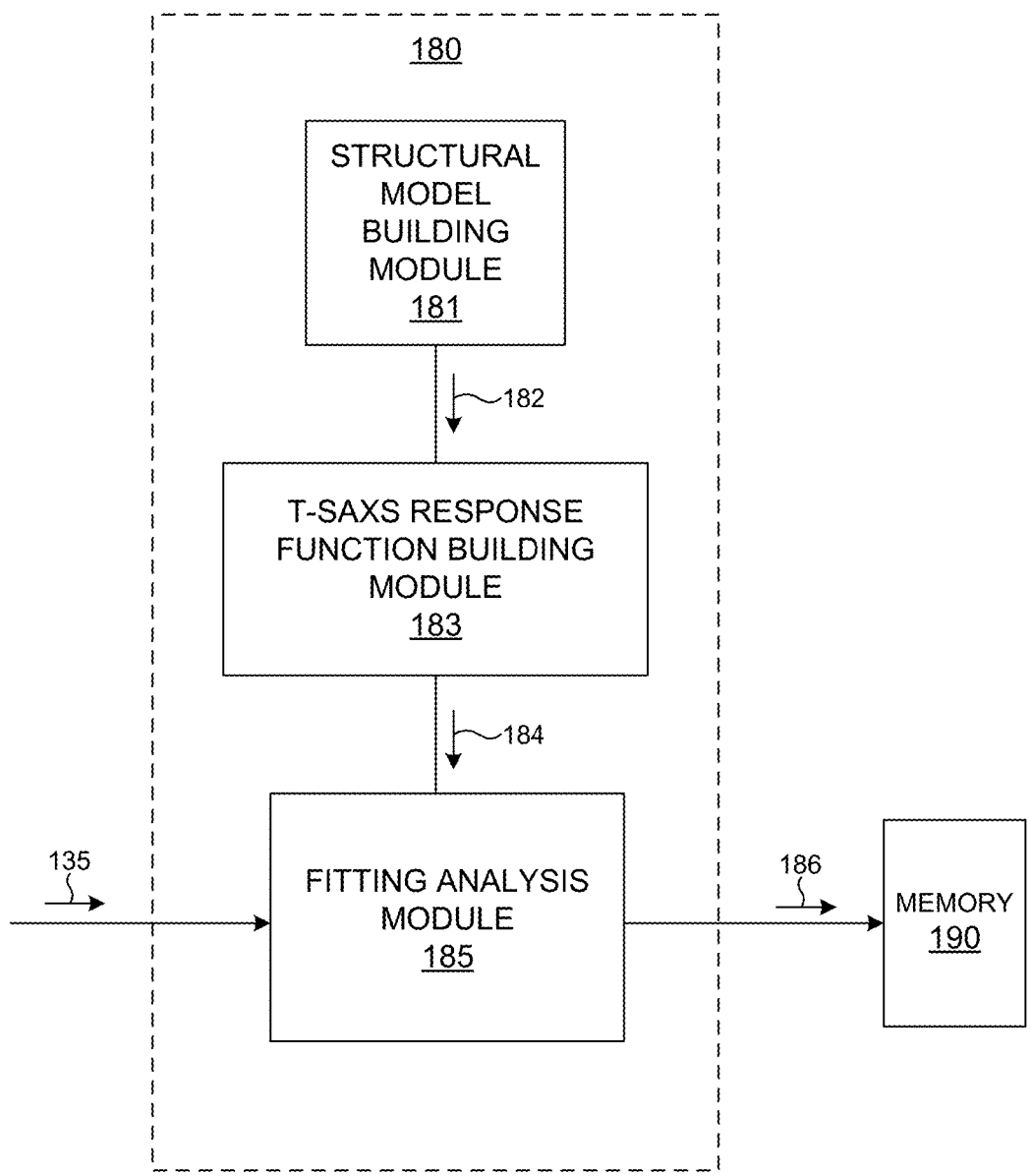
FIG. 12 is a diagram illustrative of a model building and analysis engine 180 configured to resolve specimen parameter values based on T-SAXS data in accordance with the methods described herein.

FIG. 12 is a diagram illustrative of an exemplary model building and analysis engine 180 implemented by computing system 130. As depicted in FIG. 12, model building and analysis engine 180 includes a structural model building module 181 that generates a structural model 182 of a measured structure of a specimen. In some embodiments, structural model 182 also includes material properties of the specimen. The structural model 182 is received as input to T-SAXS response function building module 183. T-SAXS response function building module 183 generates a T-SAXS response function model 184 based at least in part on the structural model 182. In some examples, the T-SAXS response function model 184 is based on x-ray form factors, $$F(\vec{q}) = \int \rho(\vec{r}) e^{-i\vec{q}\cdot\vec{r}} d\vec{r} \qquad (7)$$

where F is the form factor, q is the scattering vector, and ρ(r) is the electron density of the specimen in spherical coordinates. The x-ray scattering intensity is then given by $$I(\vec{q}) = F \cdot F. \quad (8)$$

T-SAXS response function model 184 is received as input to fitting analysis module 185. The fitting analysis module 185 compares the modeled T-SAXS response with the corresponding measured data to determine geometric as well as material properties of the specimen.

In some examples, the fitting of modeled data to experimental data is achieved by minimizing a chi-squared value. For example, for T-SAXS measurements, a chi-squared value can be defined as $$\chi^2_{SAXS} = \frac{1}{N_{SAXS}} \sum_j^{N_{SAXS}} \frac{(S_j^{SAXS\ model}(v_1,\ldots,v_L) - S_j^{SAXS\ experiment})^2}{\sigma^2_{SAXS,j}} \quad (9)$$

Where, $S_j^{SAXS\ experiment}$ is the measured T-SAXS signals 126 in the "channel" j, where the index j describes a set of system parameters such as diffraction order, energy, angular coordinate, etc. $S_j^{SAXS\ model}(v_1, \ldots, v_L)$ is the modeled T-SAXS signal $S_j$ for the "channel" j, evaluated for a set of structure (target) parameters $v_1, \ldots, v_L$, where these parameters describe geometric (CD, sidewall angle, overlay, etc.) and material (electron density, etc.). $\sigma_{SAXS,j}$ is the uncertainty associated with the jth channel. $N_{SAXS}$ is the total number of channels in the x-ray metrology. L is the number of parameters characterizing the metrology target.

Equation (9) assumes that the uncertainties associated with different channels are uncorrelated. In examples where the uncertainties associated with the different channels are correlated, a covariance between the uncertainties, can be calculated. In these examples a chi-squared value for T-SAXS measurements can be expressed as $$\chi^2_{SAXS} = \frac{1}{N_{SAXS}} \left( \vec{S}_j^{SAXS.\ model}(v_1, \ldots, v_M) - \vec{S}_j^{SAXS.\ experiment} \right)^T \quad (10)$$
$$V_{SAXS}^{-1} \left( \vec{S}_j^{SAXS.\ model}(v_1, \ldots, v_M) - \vec{S}_j^{SAXS.\ experiment} \right)$$

where, $V_{SAXS}$ is the covariance matrix of the SAXS channel uncertainties, and T denotes the transpose.

In some examples, fitting analysis module 185 resolves at least one specimen parameter value by performing a fitting analysis on T-SAXS measurement data 135 with the T-SAXS response model 184. In some examples, $\chi^2_{SAXS}$ is optimized.

As described hereinbefore, the fitting of T-SAXS data is achieved by minimization of chi-squared values. However, in general, the fitting of T-SAXS data may be achieved by other functions.

The fitting of T-SAXS metrology data is advantageous for any type of T-SAXS technology that provides sensitivity to geometric and/or material parameters of interest. Specimen parameters can be deterministic (e.g., CD, SWA, etc.) or statistical (e.g., rms height of sidewall roughness, roughness correlation length, etc.) as long as proper models describing T-SAXS beam interaction with the specimen are used.

In general, computing system 130 is configured to access model parameters in real-time, employing Real Time Critical Dimensioning (RTCD), or it may access libraries of pre-computed models for determining a value of at least one specimen parameter value associated with the specimen 101. In general, some form of CD-engine may be used to evaluate the difference between assigned CD parameters of a specimen and CD parameters associated with the measured specimen. Exemplary methods and systems for computing specimen parameter values are described in U.S. Pat. No. 7,826,071, issued on Nov. 2, 2010, to KLA-Tencor Corp., the entirety of which is incorporated herein by reference.

In some examples, model building and analysis engine 180 improves the accuracy of measured parameters by any combination of feed sideways analysis, feed forward analysis, and parallel analysis. Feed sideways analysis refers to taking multiple data sets on different areas of the same specimen and passing common parameters determined from the first dataset onto the second dataset for analysis. Feed forward analysis refers to taking data sets on different specimens and passing common parameters forward to subsequent analyses using a stepwise copy exact parameter feed forward approach. Parallel analysis refers to the parallel or concurrent application of a non-linear fitting methodology to multiple datasets where at least one common parameter is coupled during the fitting.

Multiple tool and structure analysis refers to a feed forward, feed sideways, or parallel analysis based on regression, a look-up table (i.e., "library" matching), or another fitting procedure of multiple datasets. Exemplary methods and systems for multiple tool and structure analysis is described in U.S. Pat. No. 7,478,019, issued on Jan. 13, 2009, to KLA-Tencor Corp., the entirety of which is incorporated herein by reference.

In another further aspect, an initial estimate of values of one or more parameters of interest is determined based on T-SAXS measurements performed at a single orientation of the incident x-ray beam with respect to the measurement target. The initial, estimated values are implemented as the starting values of the parameters of interest for a regression of the measurement model with measurement data collected from T-SAXS measurements at multiple orientations. In this manner, a close estimate of a parameter of interest is determined with a relatively small amount of computational effort, and by implementing this close estimate as the starting point for a regression over a much larger data set, a refined estimate of the parameter of interest is obtained with less overall computational effort.

In another aspect, metrology tool 100 includes a computing system (e.g., computing system 130) configured to implement beam control functionality as described herein. In the embodiment depicted in FIG. 1, computing system 130 is configured as a beam controller operable to control any of the illumination properties such as intensity, divergence, spot size, polarization, spectrum, and positioning of the incident illumination beam 116.

As illustrated in FIG. 1, computing system 130 is communicatively coupled to detector 119. Computing system 130 is configured to receive measurement data 135 from detector 119. In one example, measurement data 135 includes an indication of the measured response of the specimen (i.e., intensities of the diffraction orders). Based on the distribution of the measured response on the surface of detector 119, the location and area of incidence of illumination beam 116 on specimen 101 is determined by computing system 130. In one example, pattern recognition techniques are applied by computing system 130 to determine the location and area of incidence of illumination beam 116 on specimen 101 based on measurement data 135. In some examples, computing system 130 communicates command signals 137 to x-ray illumination source 110 to select the desired illumination wavelength, or redirect the x-ray emission. In some examples, computing system 130 communicates command signals 136 to beam shaping slit mechanism 120 to change the beam spot size such that incident illumination beam 116 arrives at specimen 101 with the desired beam spot size and orientation. In one example, command signals 136 cause rotary actuator 122, depicted in FIG. 5, to rotate beam shaping slit mechanism 120 to a desired orientation with respect to specimen 101. In another example, command signals 136 cause actuators associated with each of slits 126-129 to change position to reshape the incident beam 116 to a desired shape and size. In some other examples, computing system 130 communicates a command signal to wafer positioning system 140 to position and orient specimen 101 such that incident illumination beam 116 arrives at the desired location and angular orientation with respect to specimen 101.

In a further aspect, T-SAXS measurement data is used to generate an image of a measured structure based on the measured intensities of the detected diffraction orders. In some embodiments, a T-SAXS response function model is generalized to describe the scattering from a generic electron density mesh. Matching this model to the measured signals, while constraining the modelled electron densities in this mesh to enforce continuity and sparse edges, provides a three dimensional image of the sample.

Although, geometric, model-based, parametric inversion is preferred for critical dimension (CD) metrology based on T-SAXS measurements, a map of the specimen generated from the same T-SAXS measurement data is useful to identify and correct model errors when the measured specimen deviates from the assumptions of the geometric model.

In some examples, the image is compared to structural characteristics estimated by a geometric, model-based parametric inversion of the same scatterometry measurement data. Discrepancies are used to update the geometric model of the measured structure and improve measurement performance. The ability to converge on an accurate parametric measurement model is particularly important when measuring integrated circuits to control, monitor, and trouble-shoot their manufacturing process.

In some examples, the image is a two dimensional (2-D) map of electron density, absorptivity, complex index of refraction, or a combination of these material characteristics. In some examples, the image is a three dimensional (3-D) map of electron density, absorptivity, complex index of refraction, or a combination of these material characteristics. The map is generated using relatively few physical constraints. In some examples, one or more parameters of interest, such as critical dimension (CD), sidewall angle (SWA), overlay, edge placement error, pitch walk, etc., are estimated directly from the resulting map. In some other examples, the map is useful for debugging the wafer process when the sample geometry or materials deviate outside the range of expected values contemplated by a parametric structural model employed for model-based CD measurement. In one example, the differences between the map and a rendering of the structure predicted by the parametric structural model according to its measured parameters are used to update the parametric structural model and improve its measurement performance. Further details are described in U.S. Patent Publication No. 2015/0300965, the content of which is incorporated herein by reference it its entirety. Additional details are described in U.S. Patent Publication No. 2015/0117610, the content of which is incorporated herein by reference it its entirety.

In a further aspect, model building and analysis engine 180 is employed to generate models for combined x-ray and optical measurement analysis. In some examples, optical simulations are based on, e.g., rigorous coupled-wave analysis (RCWA) where Maxwell's equations are solved to calculate optical signals such as reflectivities for different polarizations, ellipsometric parameters, phase change, etc.

Values of one or more parameters of interest are determined based on a combined fitting analysis of the detected intensities of the x-ray diffraction orders at the plurality of different angles of incidence and detected optical intensities with a combined, geometrically parameterized response model. The optical intensities are measured by an optical metrology tool that may or may not be mechanically integrated with an x-ray metrology system, such as systems 100 depicted in FIG. 1. Further details are described in U.S. Patent Publication No. 2014/0019097 and U.S. Patent Publication No. 2013/0304424, the contents of each are incorporated herein by reference it their entirety.

In general, a metrology target is characterized by an aspect ratio defined as a maximum height dimension (i.e., dimension normal to the wafer surface) divided by a maximum lateral extent dimension (i.e., dimension aligned with the wafer surface) of the metrology target. In some embodiments, the metrology target under measurement has an aspect ratio of at least twenty. In some embodiments, the metrology target has an aspect ratio of at least forty.

It should be recognized that the various steps described throughout the present disclosure may be carried out by a single computer system 130 or, alternatively, a multiple computer system 130. Moreover, different subsystems of the system 100, such as the specimen positioning system 140, may include a computer system suitable for carrying out at least a portion of the steps described herein. Therefore, the aforementioned description should not be interpreted as a limitation on the present invention but merely an illustration. Further, the one or more computing systems 130 may be configured to perform any other step(s) of any of the method embodiments described herein.

In addition, the computer system 130 may be communicatively coupled to the x-ray illumination source 110, beam shaping slit mechanism 120, specimen positioning system 140, and detector 119 in any manner known in the art. For example, the one or more computing systems 130 may be coupled to computing systems associated with the x-ray illumination source 110, beam shaping slit mechanism 120, specimen positioning system 140, and detector 119, respectively. In another example, any of the x-ray illumination source 110, beam shaping slit mechanism 120, specimen positioning system 140, and detector 119 may be controlled directly by a single computer system coupled to computer system 130.

The computer system 130 may be configured to receive and/or acquire data or information from the subsystems of the system (e.g., x-ray illumination source 110, beam shaping slit mechanism 120, specimen positioning system 140, detector 119, and the like) by a transmission medium that may include wireline and/or wireless portions. In this manner, the transmission medium may serve as a data link between the computer system 130 and other subsystems of the system 100.

Computer system 130 of the metrology system 100 may be configured to receive and/or acquire data or information (e.g., measurement results, modeling inputs, modeling results, etc.) from other systems by a transmission medium that may include wireline and/or wireless portions. In this manner, the transmission medium may serve as a data link between the computer system 130 and other systems (e.g., memory on-board metrology system 100, external memory, or external systems). For example, the computing system 130 may be configured to receive measurement data (e.g., signals 135) from a storage medium (i.e., memory 132 or 190) via a data link. For instance, spectral results obtained using detector 119 may be stored in a permanent or semi-permanent memory device (e.g., memory 132 or 190). In this regard, the measurement results may be imported from on-board memory or from an external memory system. Moreover, the computer system 130 may send data to other systems via a transmission medium. For instance, specimen parameter values 186 determined by computer system 130 may be stored in a permanent or semi-permanent memory device (e.g., memory 190). In this regard, measurement results may be exported to another system.

Computing system 130 may include, but is not limited to, a personal computer system, mainframe computer system, workstation, image computer, parallel processor, or any other device known in the art. In general, the term "computing system" may be broadly defined to encompass any device having one or more processors, which execute instructions from a memory medium.

Program instructions 134 implementing methods such as those described herein may be transmitted over a transmission medium such as a wire, cable, or wireless transmission link. For example, as illustrated in FIG. 1, program instructions stored in memory 132 are transmitted to processor 131 over bus 133. Program instructions 134 are stored in a computer readable medium (e.g., memory 132). Exemplary computer-readable media include read-only memory, a random access memory, a magnetic or optical disk, or a magnetic tape.

Figure 13:
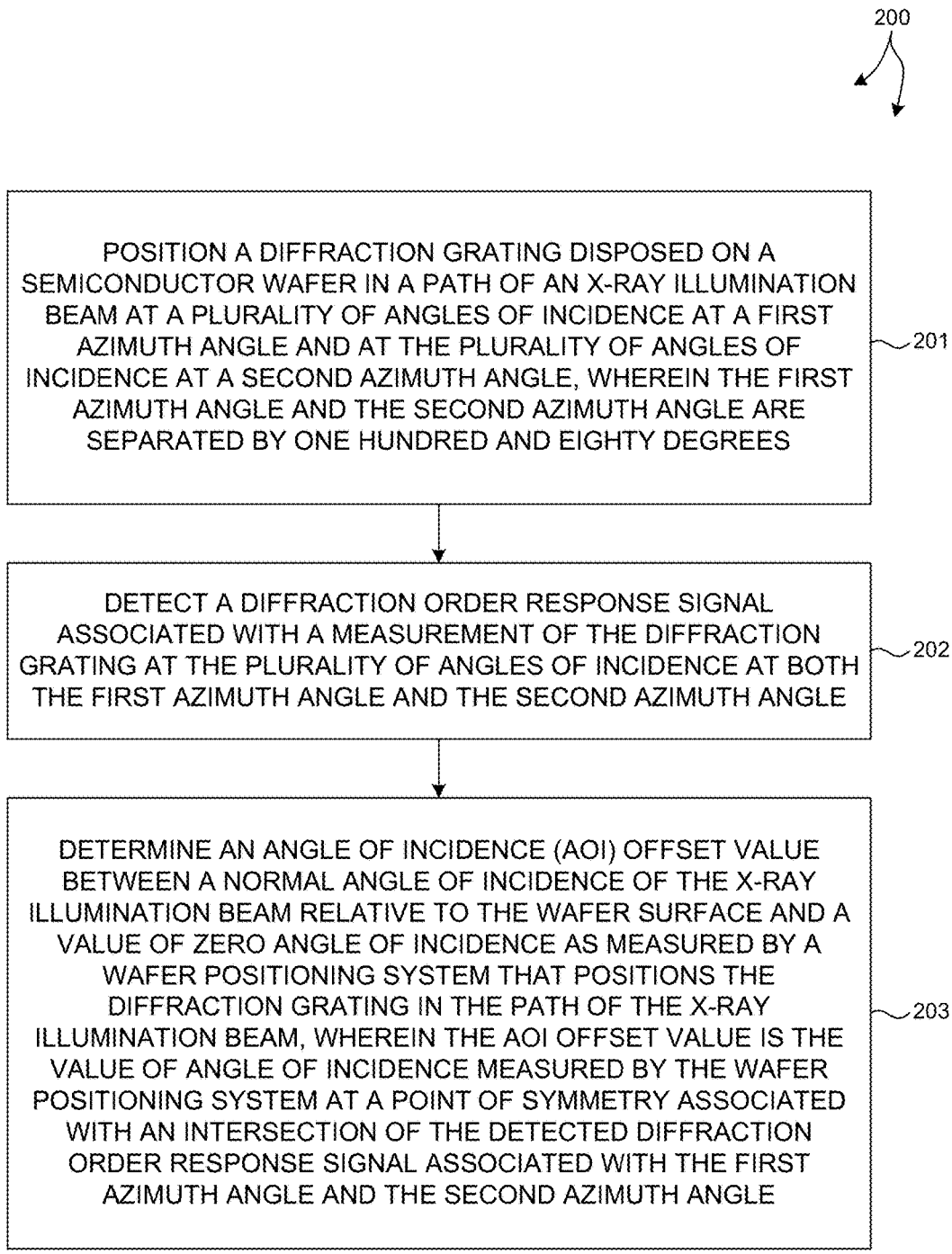
FIG. 13 depicts a flowchart illustrative of an exemplary method 200 of calibrating an angle of incidence offset value based on T-SAXS measurements at multiple angles of incidence and azimuth angles as described herein.

FIG. 13 illustrates a method 200 suitable for implementation by the metrology system 100 of the present invention. In one aspect, it is recognized that data processing blocks of method 200 may be carried out via a pre-programmed algorithm executed by one or more processors of computing system 130. While the following description is presented in the context of metrology system 100, it is recognized herein that the particular structural aspects of metrology system 100 do not represent limitations and should be interpreted as illustrative only.

In block 201, a diffraction grating disposed on a semiconductor wafer is positioned in a path of an x-ray illumination beam at a plurality of angles of incidence at a first azimuth angle and also at the plurality of angles of incidence at a second azimuth angle. The first azimuth angle and the second azimuth angle are separated by one hundred and eighty degrees.

In block 202, a diffraction order response signal associated with a measurement of the diffraction grating at the plurality of angles of incidence is detected at both the first azimuth angle and the second azimuth angle.

In block 203, an angle of incidence (AOI) offset value is determined. The AOI offset is the angle between a normal angle of incidence of the x-ray illumination beam relative to the wafer surface and a value of zero angle of incidence as measured by a wafer positioning system that positions the diffraction grating in the path of the x-ray illumination beam. The AOI offset value is the value of angle of incidence measured by the wafer positioning system at a point of symmetry associated with an intersection of the detected diffraction order response signal associated with the first azimuth angle and the second azimuth angle.

In some embodiments, scatterometry measurements as described herein are implemented as part of a fabrication process tool. Examples of fabrication process tools include, but are not limited to, lithographic exposure tools, film deposition tools, implant tools, and etch tools. In this manner, the results of a T-SAXS analysis are used to control a fabrication process. In one example, T-SAXS measurement data collected from one or more targets is sent to a fabrication process tool. The T-SAXS measurement data is analyzed as described herein and the results used to adjust the operation of the fabrication process tool.

Scatterometry measurements as described herein may be used to determine characteristics of a variety of semiconductor structures. Exemplary structures include, but are not limited to, FinFETs, low-dimensional structures such as nanowires or graphene, sub 10 nm structures, lithographic structures, through substrate vias (TSVs), memory structures such as DRAM, DRAM 4F2, FLASH, MRAM and high aspect ratio memory structures. Exemplary structural characteristics include, but are not limited to, geometric parameters such as line edge roughness, line width roughness, pore size, pore density, side wall angle, profile, critical dimension, pitch, thickness, overlay, and material parameters such as electron density, composition, grain structure, morphology, stress, strain, and elemental identification. In some embodiments, the metrology target is a periodic structure. In some other embodiments, the metrology target is aperiodic.

In some examples, measurements of critical dimensions, thicknesses, overlay, and material properties of high aspect ratio semiconductor structures including, but not limited to, spin transfer torque random access memory (STT-RAM), three dimensional NAND memory (3D-NAND) or vertical NAND memory (V-NAND), dynamic random access memory (DRAM), three dimensional FLASH memory (3D-FLASH), resistive random access memory (Re-RAM), and phase change random access memory (PC-RAM) are performed with T-SAXS measurement systems as described herein.

As described herein, the term "critical dimension" includes any critical dimension of a structure (e.g., bottom critical dimension, middle critical dimension, top critical dimension, sidewall angle, grating height, etc.), a critical dimension between any two or more structures (e.g., distance between two structures), and a displacement between two or more structures (e.g., overlay displacement between overlaying grating structures, etc.). Structures may include three dimensional structures, patterned structures, overlay structures, etc.

As described herein, the term "critical dimension application" or "critical dimension measurement application" includes any critical dimension measurement.

As described herein, the term "metrology system" includes any system employed at least in part to characterize a specimen in any aspect, including critical dimension applications and overlay metrology applications. However, such terms of art do not limit the scope of the term "metrology system" as described herein. In addition, the metrology systems described herein may be configured for measurement of patterned wafers and/or unpatterned wafers. The metrology system may be configured as a LED inspection tool, edge inspection tool, backside inspection tool, macro-inspection tool, or multi-mode inspection tool (involving data from one or more platforms simultaneously), and any other metrology or inspection tool that benefits from the measurement techniques described herein.

Various embodiments are described herein for a semiconductor processing system (e.g., an inspection system or a lithography system) that may be used for processing a specimen. The term "specimen" is used herein to refer to a wafer, a reticle, or any other sample that may be processed (e.g., printed or inspected for defects) by means known in the art.

As used herein, the term "wafer" generally refers to substrates formed of a semiconductor or non-semiconductor material. Examples include, but are not limited to, monocrystalline silicon, gallium arsenide, and indium phosphide. Such substrates may be commonly found and/or processed in semiconductor fabrication facilities. In some cases, a wafer may include only the substrate (i.e., bare wafer). Alternatively, a wafer may include one or more layers of different materials formed upon a substrate. One or more layers formed on a wafer may be "patterned" or "unpatterned." For example, a wafer may include a plurality of dies having repeatable pattern features.

A "reticle" may be a reticle at any stage of a reticle fabrication process, or a completed reticle that may or may not be released for use in a semiconductor fabrication facility. A reticle, or a "mask," is generally defined as a substantially transparent substrate having substantially opaque regions formed thereon and configured in a pattern. The substrate may include, for example, a glass material such as amorphous $SiO_2$. A reticle may be disposed above a resist-covered wafer during an exposure step of a lithography process such that the pattern on the reticle may be transferred to the resist.

One or more layers formed on a wafer may be patterned or unpatterned. For example, a wafer may include a plurality of dies, each having repeatable pattern features. Formation and processing of such layers of material may ultimately result in completed devices. Many different types of devices may be formed on a wafer, and the term wafer as used herein is intended to encompass a wafer on which any type of device known in the art is being fabricated.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, XRF disc, digital versatile disc (DVD), floppy disk and blu-ray disc where disks usually reproduce data magnetically, while discs reproduce data optically with lasers. Combinations of the above should also be included within the scope of computer-readable media.

Although certain specific embodiments are described above for instructional purposes, the teachings of this patent document have general applicability and are not limited to the specific embodiments described above. Accordingly, various modifications, adaptations, and combinations of various features of the described embodiments can be practiced without departing from the scope of the invention as set forth in the claims.

What is claimed is:

1. A metrology system comprising:
an x-ray illumination source configured to generate an x-ray illumination beam;
a specimen stage moveable in a first direction orthogonal to an axis of the x-ray illumination beam and a second direction orthogonal to the axis of the x-ray illumination beam;
a specimen moveably attached to the specimen stage;
a first occlusion element disposed on the specimen stage adjacent to a specimen, the first occlusion element having a central axis co-planar with the surface of the specimen, wherein the specimen stage in a first position locates the first occlusion element in a path of the x-ray illumination beam such that a portion of the x-ray illumination beam is occluded by the first occlusion element;
a second occlusion element disposed on the specimen stage adjacent to the specimen, the second occlusion element having a central axis co-planar with the surface of the specimen and aligned in a direction different from the central axis of the first occlusion element, wherein the specimen stage in a second position locates the second occlusion element in the path of the x-ray illumination beam such that a portion of the x-ray illumination beam is occluded by the second occlusion element;
an x-ray detector configured to detect a first amount of transmitted flux at the first position and a second amount of flux at the second position; and
a computing system configured to determine a first position of the first occlusion element with respect to the x-ray illumination beam in the first direction based on the first amount of transmitted flux and determine a second position of the the second occlusion element with respect to the x-ray illumination beam in the second direction based on the second amount of transmitted flux.

2. The metrology system of claim 1, wherein the determining of the first and second positions is based on a model of transmitted flux as a function of position of the first and second occlusion elements with respect to the x-ray illumination beam.

3. The metrology system of claim 1, wherein any of the first and second occlusion elements is cylindrically shaped.

4. The metrology system of claim 1, wherein any of the first and second occlusion elements includes a knife edge, wherein the central axis is aligned with the knife edge.

5. The metrology system of claim 1, wherein any of the first and second occlusion elements includes one or more planar surfaces extending in a direction parallel to the central axis.

6. The metrology system of claim 1, further comprising:
an alignment camera that generates a first image of at least a portion of the first occlusion element at the first position and a second image of at least a portion of the second occlusion element in at the second position.

7. The metrology system of claim 6, wherein the portion of the first occlusion element includes a first fiducial mark located co-planar with the central axis of the first occlusion element, and wherein the portion of the second occlusion element includes a second fiducial mark located co-planar with the central axis of the second occlusion element.

8. The metrology system of claim 6, wherein the specimen stage moves to a third position with respect to the x-ray illumination beam such that a fiducial mark disposed on the specimen is within the field of view of the alignment camera, and wherein a location of incidence of the x-ray illumination beam on the specimen is determined at the third position based on the first and second images.

9. The metrology system of claim 6, wherein the alignment camera includes an auto-focus mechanism that maintains a sharp image focus by moving a focal plane of the alignment camera by a precisely measured distance, and wherein the alignment camera measures a change in distance between a reference frame and the surface of the specimen at different locations on the surface of the specimen.

10. The metrology system of claim 9, wherein a relative position of the specimen with respect to the first occlusion element in the direction normal to the surface of the specimen is measured based on the autofocus mechanism, and wherein the specimen positioning system moves the specimen in the direction normal to the surface of the specimen such that the relative position is a negligible value.

11. The metrology system of claim 1, further comprising:
one or more proximity sensors configured to measure a distance between a reference frame and the surface of the specimen at each of a plurality of different locations on a back side surface of the specimen opposite the surface of the specimen.

12. A metrology system comprising:
an x-ray illumination source configured to generate an x-ray illumination beam;
a specimen positioning system configured to position a specimen with respect to the x-ray illumination beam such that the x-ray illumination beam is incident on the surface of the specimen at any location on the surface of the specimen and rotate the specimen about an axis of rotation with respect to the x-ray illumination beam such that the x-ray illumination beam is incident on the surface of the specimen at any location at a plurality of angles of incidence;
an occlusion element disposed adjacent to the specimen, the occlusion element having a central axis co-planar with the surface of the specimen;
an x-ray detector configured to detect an amount of transmitted flux over a range of angular positions of the axis of rotation, wherein at least a portion of the x-ray illumination beam is incident on the occlusion element over the range of angular positions; and
a computing system configured to determine an adjustment of a position of the axis of rotation with respect to the x-ray illumination beam based on the detected amount of transmitted flux.

13. The metrology system of claim 12, wherein the computing system is further configured to determine an adjustment of a position of the specimen with respect to the axis of rotation based on the detected amount of transmitted flux.

14. The metrology system of claim 13, wherein the adjustment of position of the axis of rotation and the adjustment of position of the specimen reduce a movement of the occlusion element with respect to the x-ray illumination beam over the range of angular positions.

15. The metrology system of claim 13, wherein the adjustment of the position of the axis of rotation and the adjustment of the position of the specimen are based on a model of transmitted flux as a function of position of the occlusion element with respect to the x-ray illumination beam over the range of angular positions.

16. The metrology system of claim 13, wherein the detecting of the amount of transmitted flux over the range of angular positions and the determining of the adjustment of the position of the axis of rotation and the adjustment of the position of the specimen based on the detected amount of transmitted flux are performed iteratively.

17. The metrology system of claim 12, wherein the x-ray detector is further configured to detect a second amount of transmitted flux over a second range of angular positions of the rotational axis, wherein the x-ray illumination beam is incident on an unpatterned area of the specimen, and wherein the computing system is further configured to determine an offset value associated with the angular position of the rotational axis based on the second amount of detected flux.

18. The metrology system of claim 17, wherein the determining of the offset value involves a fitting of an absorption model to the second amount of detected flux over the second range of angular positions.

19. A method comprising:
positioning a diffraction grating disposed on a semiconductor wafer in a path of an x-ray illumination beam at a plurality of angles of incidence at a first azimuth angle and at the plurality of angles of incidence at a second azimuth angle, wherein the first azimuth angle and the second azimuth angle are separated by one hundred and eighty degrees;
detecting a diffraction order response signal associated with a measurement of the diffraction grating at the plurality of angles of incidence at both the first azimuth angle and the second azimuth angle; and
determining an angle of incidence (AOI) offset value between a normal angle of incidence of the x-ray illumination beam relative to the wafer surface and a value of zero angle of incidence as measured by a wafer positioning system that positions the diffraction grating in the path of the x-ray illumination beam, wherein the AOI offset value is the value of angle of incidence measured by the wafer positioning system at a point of symmetry associated with an intersection of the detected diffraction order response signal associated with the first azimuth angle and the second azimuth angle.

20. The method of claim 19, wherein the diffraction grating includes a periodic structure oriented at an oblique angle with respect to a surface of the semiconductor wafer.

21. The method of claim 20, further comprising:
determining a value of the oblique angle as a difference between a first value of angle of incidence measured by the wafer positioning system associated with a peak value of the detected diffraction order response signal associated with either the first azimuth angle or the second azimuth angle and a second value of angle of incidence measured by the wafer positioning system associated with the point of symmetry.

22. The method of claim 19, wherein the diffraction order response signal includes signal information associated with multiple diffraction orders.

* * * * *